(12) United States Patent
Carabajal

(10) Patent No.: US 10,856,884 B2
(45) Date of Patent: Dec. 8, 2020

(54) WEARABLE EMERGENCY HEMORRHAGE CESSATION SYSTEMS

(71) Applicant: Johnny Xavier Carabajal, Huntington Beach, CA (US)

(72) Inventor: Johnny Xavier Carabajal, Huntington Beach, CA (US)

( * ) Notice: Subject to any disclaimer, the term of this patent is extended or adjusted under 35 U.S.C. 154(b) by 92 days.

(21) Appl. No.: 15/749,055

(22) PCT Filed: Jul. 26, 2016

(86) PCT No.: PCT/US2016/044071
§ 371 (c)(1),
(2) Date: Jan. 30, 2018

(87) PCT Pub. No.: WO2017/023619
PCT Pub. Date: Feb. 9, 2017

(65) Prior Publication Data
US 2018/0214161 A1    Aug. 2, 2018

Related U.S. Application Data

(60) Provisional application No. 62/333,189, filed on May 7, 2016, provisional application No. 62/199,432, filed on Jul. 31, 2015.

(51) Int. Cl.
*A61B 17/135* (2006.01)
*A61B 17/132* (2006.01)
(Continued)

(52) U.S. Cl.
CPC ........ *A61B 17/1355* (2013.01); *A61B 5/0036* (2018.08); *A61B 5/0205* (2013.01);
(Continued)

(58) Field of Classification Search
CPC . A61B 5/02042; A61B 5/0205; A61B 5/4836; A61B 5/6802; A61B 5/746;
(Continued)

(56) References Cited

U.S. PATENT DOCUMENTS 3,080,867 A    3/1963  Eichinger
4,321,929 A *  3/1982  Lemelson .......... A61B 17/1355
                                                      600/301
(Continued)

FOREIGN PATENT DOCUMENTS

EP            777442 B1    11/1999
WO       1992005741 A1     4/1992
WO       2015193847 A1    12/2015

OTHER PUBLICATIONS

Selvaraj, et al, A novel approach using time-frequency analysis of pulse-oximeter data to detect progressive hypovolemia in spontaneously breathing healthy subjects, IEEE Trans Biomed Eng. Aug. 2011, 58(8), doi: 10.1109/TBME.2011.2144981. Epub Apr. 21, 2011.

(Continued)

*Primary Examiner* — George J Ulsh
(74) *Attorney, Agent, or Firm* — Total Awareness Consulting Services; Robert Winslow

(57) ABSTRACT

A wearable system comprises tourniquets. Each of the tourniquets comprises an inflatable chamber, and is configured to occlude blood flow in an artery of a wearer. The wearable system comprises compressed gas sources in fluid communication with the inflatable chamber of the tourniquets. The wearable system comprises valves. Each of the valves comprises an input in fluid communication with one of the compressed gas sources, and an output in fluid communication with the inflatable chamber of one of the tourniquets. The wearable system comprises fixed pressure regulators. Each of the fixed pressure regulators is in fluid (Continued)

communication with the valves, and is configured to regulate a pressure of the compressed gases delivered to the inflatable chamber of at least one of the tourniquets. The wearable system comprises switches. Each of the switches is configured to operate one of the valves.

14 Claims, 26 Drawing Sheets

(51) Int. Cl.
| | |
|---|---|
| A61B 5/00 | (2006.01) |
| A61B 5/02 | (2006.01) |
| A61B 5/0205 | (2006.01) |
| A61B 17/00 | (2006.01) |
| F41H 1/02 | (2006.01) |
| A61B 5/021 | (2006.01) |
| A61B 5/026 | (2006.01) |
| A61B 5/024 | (2006.01) |

(52) U.S. Cl.
CPC ........ *A61B 5/02042* (2013.01); *A61B 5/4836* (2013.01); *A61B 5/6802* (2013.01); *A61B 5/746* (2013.01); *A61B 17/1322* (2013.01); A61B 5/0022 (2013.01); A61B 5/021 (2013.01); A61B 5/024 (2013.01); A61B 5/026 (2013.01); A61B 5/0531 (2013.01); A61B 2017/00026 (2013.01); A61B 2017/00044 (2013.01); A61B 2017/00084 (2013.01); A61B 2017/00115 (2013.01); A61B 2017/00199 (2013.01); A61B 2017/00203 (2013.01); A61B 2017/00207 (2013.01); A61B 2017/00221 (2013.01); *F41H 1/02* (2013.01)

(58) Field of Classification Search
CPC ............ A61B 17/1322; A61B 17/1355; A61B 5/0022; A61B 5/021; A61B 5/024; A61B 5/026; A61B 5/0531; A61B 2017/00026; A61B 2017/00044; A61B 2017/00084; A61B 2017/00115; A61B 2017/00199; A61B 2017/00203; A61B 2017/00207; A61B 2017/00221; A61B 17/135; F41H 1/02

See application file for complete search history.

(56) References Cited

U.S. PATENT DOCUMENTS

| | | | |
|---|---|---|---|
| 5,234,459 A | 8/1993 | Lee | |
| 6,007,559 A * | 12/1999 | Arkans | A61B 17/135 601/150 |
| 6,299,629 B1 | 10/2001 | Gruenfeld et al. | |
| 6,746,470 B2 | 6/2004 | McEwen et al. | |
| 7,604,651 B1 * | 10/2009 | Harris | A41D 13/1236 606/203 |
| 7,872,575 B2 | 1/2011 | Tabe | |
| 7,909,849 B2 | 3/2011 | McEwen | |
| 9,113,895 B2 | 8/2015 | McEwen et al. | |
| 9,138,236 B2 | 9/2015 | McEwen et al. | |
| 2007/0191881 A1 | 8/2007 | Amisar et al. | |
| 2008/0281351 A1 * | 11/2008 | Croushorn | A61B 17/1325 606/202 |
| 2010/0211096 A1 | 8/2010 | McEwen et al. | |
| 2014/0260939 A1 | 9/2014 | Neal | |
| 2014/0336697 A1 * | 11/2014 | Masaki | A61B 17/135 606/203 |
| 2016/0058653 A1 | 3/2016 | Oberdier | |

OTHER PUBLICATIONS

ARMR Systems Webpage, http://armrsystems.com/technology/, Jan. 27, 2018.
Adam Tourniquet, M.A.S. Med Global page, Rishon StartUp website, http://www.rishonlezion.muni.il/rishonstartup/English//Lists/Startups%20and%20Mentors/DispForm.aspx?ID=29, Jan. 27, 2018.
Adam Intelligent Tourniquet System YouTube Video, https://youtu.be/9UUou8nu36o, Jun. 28, 2016.

* cited by examiner

WEARABLE EMERGENCY HEMORRHAGE CESSATION SYSTEMS

CROSS-REFERENCE TO RELATED APPLICATIONS

This application claims the benefit of U.S. Provisional Application No.: 62/199,432, filed Jul. 31, 2015, U.S. Provisional Application No.: 62/333,189, filed May 7, 2016, and International Application No. PCT/US2016/044071, filed Jul. 26, 2016, which are hereby incorporated by reference in their entirety.

BACKGROUND

Hemorrhage is the leading cause of combat deaths. In many cases, applying a tourniquet after sustaining a wound in an appendage or at a junction is too painful to apply effectively. In some cases, a person, such as an injured soldier, law enforcement officer, or government agent loses consciousness and is unable to apply self-aid. Self-aid on multiple extremities is unlikely in most battleground cases since each solder is typically issued one tourniquet. In many cases, medical personnel cannot reach a wounded soldier, law enforcement officer, or government agent in time to cease a hemorrhage.

Many existing tourniquets require manual operation. Manual operation of a tourniquet by a person such as, for example, a soldier, law enforcement officer, or government agent who has been critically injured is often too difficult to complete effectively. In some cases, a person may be trapped and cannot effectively apply self-aid to cease a hemorrhage. Manual operation of a tourniquet by medical personnel may take too much time in cases involving mass injuries such as, for example, on a battlefield, in a terrorist attack, in a natural disaster, and after a multivehicle accident.

Many existing tourniquets do not provide the durability and/or the wearability necessary for effective combat and/or immediate use. Many existing tourniquets are difficult to operate while wearing gloves. Many existing tourniquets require operation that causes excessive noise which could give away the position of an injured soldier, law enforcement officer, or government agent. Many existing tourniquets do not apply enough pressure to completely occlude blood flow in the artery of the wearer.

What is needed is a system, device, and/or method to effectively cause cessation of hemorrhages.

DETAILED DESCRIPTION OF EMBODIMENTS

Figure 1A:
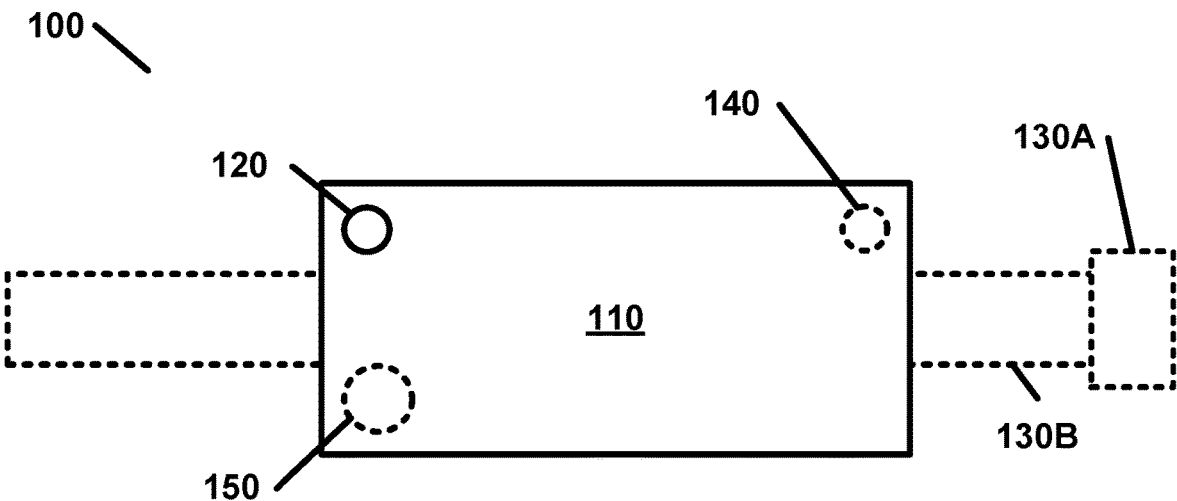
FIGS. 1A, 1B, and 1C illustrate examples of tourniquets as per aspects of various embodiments.

Embodiments are configured to cause cessation of hemorrhages.

Some of the various embodiments may comprise a wearable system. The wearable system may comprise at least one tourniquet. Each of the at least one tourniquet may comprise an inflatable chamber. An inflatable chamber may comprise materials such as, for example, polyurethane coated nylon, Kevlar, Anso-tex, combinations thereof, and/or the like. Each of the at least one tourniquet may be configured to occlude blood flow in at least one artery of a wearer. The wearable system may comprise at least one compressed gas source. The at least one compressed gas source may be in fluid communication with the inflatable chamber of at least one of the at least one tourniquet. The at least one compressed gas source may be at least a part of at least one wearable component of the wearable system. The wearable system may comprise at least one valve. Each of the at least one valve may comprise an input in fluid communication with at least one of the at least one compressed gas source. Each of the at least one valve may comprise an output in fluid communication with the inflatable chamber of the at least one of the at least one tourniquet. The wearable system may comprise at least one fixed pressure regulator. Each of the at least one fixed pressure regulator may be in fluid communication with the at least one valve. Each of the at least one fixed pressure regulator may be configured to regulate a pressure of at least one compressed gas delivered to the inflatable chamber of the at least one of the at least one tourniquet. The wearable system may comprise at least one switch. Each of the at least one switch may be configured to operate one of the at least one valve. At least one of the at least one switch may be configured for mechanical operation. At least one of the at least one switch may be configured to mechanically operate at least one of the at least one valve. At least one of the at least one switch may be configured to operate the at least one valve after at least one of the at least one tourniquet is fitted to the wearer.

According to some of the various embodiments, each of at least one tourniquet may be configured to remain in place during inflation. Each of the at least one tourniquet may comprise at least one adjustable component. The at least one adjustable component may be distinct from an inflatable chamber. The at least one adjustable component may comprise a strap, a cable, a cord, a buckle, a clamp, a ring, combinations thereof, and/or the like. Examples of a strap include webbing made from cotton, nylon, polypropylene, rubber, combinations thereof, and/or the like. Examples of a buckle include a ladder lock, tri-glide, side release buckle, cam buckle, moving bar buckle, combinations thereof, and/or the like. Examples of a ring include a square ring, a D ring, a sewable loop, combinations thereof, and/or the like. According to some of the various embodiments, each of the at least one tourniquet may comprise a sleeve. The sleeve may be configured to contain the inflatable chamber. The sleeve may comprise Kevlar, at least one fiber material, at least one shape memory alloy, at least one ballistic and fragmentation resistant material, at least one ripstop fabric, nylon, combinations thereof, and/or the like. The sleeve may be at least partially filled with a powder configured to prevent a first portion of the inflatable chamber from sticking to a second portion of the inflatable chamber when deflated. The at least one tourniquet may be at least partially coupled to a suit, a uniform, a piece of body armor, an article of clothing, combinations thereof, and/or the like. For example, the at least one tourniquet may be at least partially attached or inserted into a sleeve. The sleeve may be at least partially attached to a suit, uniform, article of clothing, combinations thereof, and/or the like. In another example, the at least one tourniquet may be inserted into a pocket that may be at least partially attached to a piece of body armor. Examples of a suit include a flight suit, space suit, wetsuit, business suit (e.g. those worn by government agents), combinations thereof, and/or the like. In the aforementioned examples, the at least one tourniquet may be configured to be operable as a Personal Floatation Device (PFD). Employment as a PFD may require loosening at least one adjustable component. Employment as a PFD may comprise activation of at least one switch configured to cause inflation of the inflatable chamber of at least one tourniquet. Examples of a uniform include uniforms configured for employment by a soldier, government official, law enforcement officer, combinations thereof, and/or the like. Examples of a piece of body armor include a drop leg holster, shoulder pad, cummerbund, combinations thereof, and/or the like. Examples of an article of clothing include hunting clothing and tactical clothing.

According to some of the various embodiments, at least one of at least one tourniquet may be configured to be employed around an arm, a forearm, an upper arm, a leg, a lower leg, an upper leg, combinations thereof, and/or the like. At least one of the at least one tourniquet may be configured for employment to occlude blood flow in a radial artery, ulnar artery, brachial artery, anterior tibial artery, posterior tibial artery, peroneal artery, femoral artery, combinations thereof, and/or the like. At least one of the at least one tourniquet may be configured for employment as a junctional tourniquet at a shoulder, abdomen, and a groin. The junctional tourniquet may be disposed to a rigid structure such as, for example, body armor, a vest, a cummerbund, a belt, combinations thereof, and/or the like. At least one of the at least one tourniquet may be configured to be employed to occlude blood flow in a subclavian artery, axillary artery, abdominal aortic artery, external iliac artery, internal iliac artery, combinations thereof, and/or the like. The wearable system may comprise a multitude of tourniquets, for example, up to 13 tourniquets.

According to some of the various embodiments, an inflatable chamber may be coupled to a pressure release valve. The pressure release valve may be configured to release excess pressure from the inflatable chamber. For example, during flight evacuation, the pressure release valve may be configured to release excess pressure when gaining altitude. A valve that has been activated may be configured to cause pressure to be maintained in the inflatable chamber during a drop in altitude. The inflatable chamber may be coupled to a dump valve configured to dump air out of the inflatable chamber. The dump valve may, according to various embodiments, be activated by: the wearer, the system, a remote device, another person, combinations thereof, and/or the like.

According to some of the various embodiments, a compressed gas source may comprise at least one pressurized container. A compressed gas source may comprise at least one gas cartridge. The at least one gas cartridge may comprise a threaded end and/or a non-threaded end. The at least one gas cartridge may comprise at least one $CO_2$ cartridge. The at least one gas cartridge may be punctured upon opening a cover of a control unit, removing a retaining pin disposed to a cover of a control unit, activation of at least one switch, activation of at least one valve, combinations thereof, and/or the like. The at least one compressed gas source may comprise at least one gas in liquid form. The at least one compressed gas source may comprise at least one element in addition to gas(es) such as at least one powder.

According to some of the various embodiments, at least one fixed pressure regulator may be configured for a distinct maximum pressure for at least one tourniquet configured for an arm of a wearer, a leg of a wearer, a forearm of a wearer, an upper arm of a wearer, a lower leg of a wearer, an upper leg of a wearer, a shoulder of a wearer, a groin of a wearer, the abdomen of a wearer, combinations thereof, and/or the like. The at least one fixed pressure regulator may be set within a range of, for example, 6-10 PSI or 310-415 mm Hg. For example, a tourniquet may require pressurization up to 7 PSI to effectively occlude blood flow in an arm or leg of the wearer. For example, a tourniquet may require pressurization up to 9 PSI to effectively occlude blood flow in a shoulder or groin of the wearer. For example, a tourniquet may require pressurization up to 10 PSI to effectively occlude blood flow in the abdomen of the wearer.

According to some of the various embodiments, at least one switch may comprise a toggle switch, a button, a solenoid, a pull cord, combinations thereof, and/or the like. The at least one switch may be configured for one step operation and/or a quiet operation. The at least one switch may be configured to present a visual indicator of operation. The button may be configured as a push-button. The button may comprise a mechanical linkage. The button may comprise electronics. The button may be configured to visually indicate a position (e.g. on or off; activated or inactive). The at least one switch may comprise a momentary switch. The at least one switch may comprise an on/off switch. The at least one switch may be configured for mechanical and/or electronical operation. The at least one switch may be coupled to a cover configured to prevent accidental activation of the switch. The cover may be hinged. The cover may comprise a transparent material.

According to some of the various embodiments, a wearable system may comprise a manifold. The manifold may comprise at least three ports. Each of at least two of the at least three ports may be in fluid communication with one of at least one tourniquet. At least one of the at least three ports may be in fluid communication with an inflatable cervical collar. At least one of the at least three ports may be in fluid communication with one of at least one inflatable splint. The manifold may comprise at least one valve chamber. Each of the at least one valve chamber may be configured to accept one of at least one valve. Each of the at least one valve may be mechanically and/or electrically operated by one of at least one switch. The manifold may comprise at least one compressed gas source. The manifold may be pressurized with the at least one compressed gas source at a factory.

According to some of the various embodiments, a wearable system may comprise at least one check valve. Each of the at least one check valve may be in fluid communication with an inflatable chamber of one of at least one tourniquet. Each of the at least one check valve may be configured to prevent loss of at least a portion of pressure in the inflatable chamber when pressurized. For example, when a fluid conduit is cut or damaged, at least one check valve may be configured to keep the inflatable chamber at least partially pressurized. According to some of the various embodiments, the at least one check valve may be configured with a shut off pressure that may be less than or equal to the pressure of one of at least one fixed pressure regulator. An example of a fluid conduit comprises flexible pneumatic tubing. The flexible pneumatic tubing may be covered in a sheath, a sleeve, and/or the like. The sheath and/or sleeve may comprise nylon, plastic, hollow cord (e.g. parachute cord), combinations thereof, and/or the like. Other examples of a fluid conduit may comprise tubes and/or channels comprising metal, plastic, carbon fiber, at least one ballistic and fragmentation resistant material, combinations thereof, and/or the like.

According to some of the various embodiments, a wearable system may comprise at least one physiological sensor. The at least one physiological sensor may be configured to measure heart rate, blood flow, blood pressure, oxygen saturation, skin conductance, combinations thereof, and/or the like of a wearer. Examples of a physiological sensor include a heart rate sensor, a blood pressure sensor, a temperature sensor, a conductance sensor, a flow sensor, an oxygen saturation sensor, combinations thereof, and/or the like. According to some of the various embodiments, the wearable system may comprise at least one processing unit. The at least one processing unit may be configured to receive at least one physiological signal from the at least one physiological sensor. The at least one processing unit may be configured to communicate at least one command to at least one of at least one switch. The at least one command may be based at least in part on at least one of the at least one physiological signal. The at least one processing unit may be configured to record a time stamp associated with activation of each of at least one switch. For example, if a physiological signal comprising a pulse rate communicates a drop or loss of pulse in a location (e.g. an appendage), the at least one command may comprise an electrical signal configured to operate a valve (e.g. solenoid) configured to activate inflation of at least one tourniquet associated with (i.e. proximal to) the location. In this example, a manifold may comprise the at least one valve (solenoid). According to some of the various embodiments, the wearable system may comprise a plurality of physiological sensors. At least two of the plurality of physiological sensors may be configured to communicate a physiological signal associated with a distinct location on the body of the wearer. For example, at least one of the plurality of physiological sensors may be associated with each of at least two appendages. In another example, each of the plurality of physiological sensors may be associated with one appendage.

According to some of the various embodiments, a wearable system may comprise a receiving unit. The receiving unit may be configured to receive at least one command. The at least one command may be wirelessly communicated from a remote device. Examples of a remote device include a mobile device (e.g. a smartphone, a smartwatch, a tablet, etc.), an unmanned vehicle, a satellite, a server, combinations thereof, and/or the like. The remote device may, for example, be operated by a wearer, a second party, a soldier, an officer of the law, a government agent, combinations thereof, and/or the like. According to some of the various embodiments, the remote device may be coupled to an accessory device. The accessory device may be configured to present a user interface on the accessory device and/or on a display of the remote device. The user interface may comprise at least one operational control. The at least one operational control may be presented to operate similarly to at least one switch. The accessory device may be configured as a security key. Coupling of the accessory device to the remote device may be employed prior to communicating commands to the receiving unit of the wearable system. The remote device may be configured to communicate a distress signal when coupled to the accessory device.

According to some of the various embodiments, a wearable system may comprise at least one wireless transmitter and at least one wireless receiver. One of the at least one wireless transmitter may be coupled to one of the at least one physiological sensor. Each of at least some of a plurality of wireless transmitters may be coupled to each of a plurality of physiological sensors. At least one of the at least one wireless receiver may be coupled to a processing unit. At least one of the at least one wireless transmitter may be configured to broadcast physiological signals to at least one remote device. At least one of the at least one wireless transmitter may be configured to broadcast at least one baseline associated with at least one physiological signal. The at least one baseline may comprise a mean and/or mode of values associated with historic physiological information. The wearable system may be configured to broadcast a wearer profile comprising medical information to at least one remote device. Physiological signals, wireless broadcasts, and/or wireless communication with a remote device may be encrypted.

According to some of the various embodiments, a wearable system may be configured to accept voice commands from a wearer through employment of at least one microphone in communication with a voice recognition and/or voice command system. Voice commands may require validation by the wearer. Validation may comprise a password, activation of at least one switch, at least one biometric identifier from the wearer, combinations thereof, and/or the like. The wearable system may be configured to accept gesture commands from the wearer through employment of at least one camera in communication with a gesture recognition and/or gesture command system. Gesture commands may require validation by the wearer. Validation may comprise an additional gesture.

FIG. 1A illustrates an example of a tourniquet as per an aspect of various embodiments. Tourniquet 100 may comprise an inflatable chamber 110. The inflatable chamber 110 may be in fluid communication with a fluid conduit through employment of a fluid conduit port 120. The tourniquet 100 may comprise at least one adjustable component (e.g. 130A and/or 130B). The at least one adjustable component (e.g. 130A and/or 130B) may be distinct from the inflatable chamber 110. The inflatable chamber may be in fluid communication with a pressure release valve 140. The inflatable chamber may be in fluid communication with a dump valve 150.

Figure 1B:
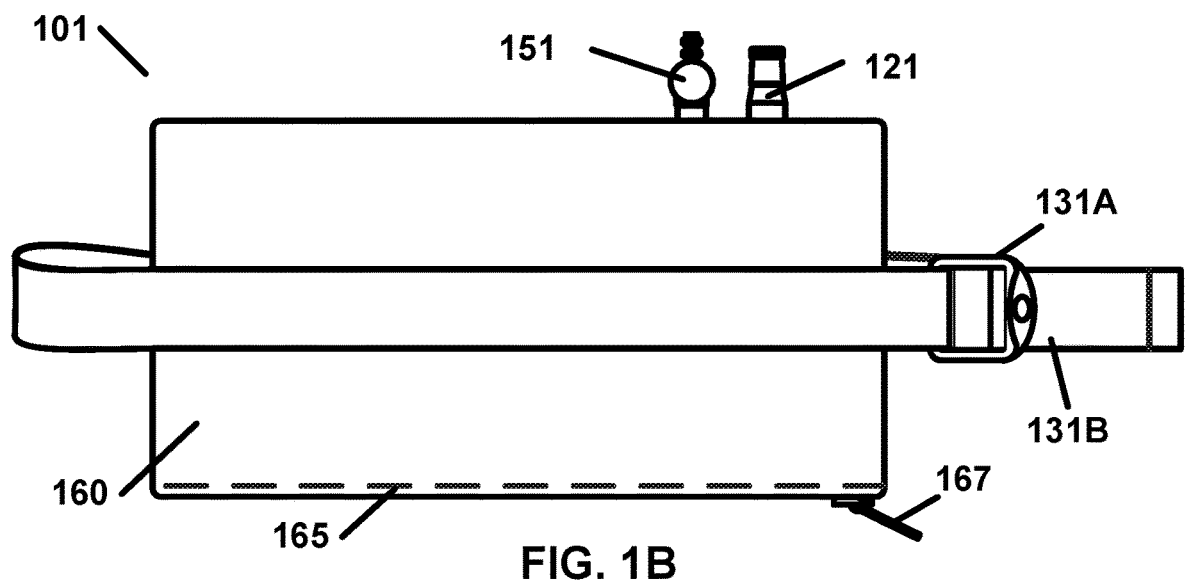

FIG. 1B illustrates an example of a tourniquet as per an aspect of an embodiment. A tourniquet 101 may comprise a sleeve 160 configured to contain an inflatable chamber. The inflatable chamber may be secured in the sleeve through employment of zipper 165. Zipper 165 may be opened and closed by zipper pull 167. The inflatable chamber may be in fluid communication with a fluid conduit through employment of a fluid conduit port 121. The tourniquet 101 may comprise at least one adjustable component (e.g. 131A and/or 131B). The at least one adjustable component (e.g. 131A and/or 131B) may be distinct from the inflatable chamber. The inflatable chamber may be in fluid communication with a dump valve 151.

Figure 1C:
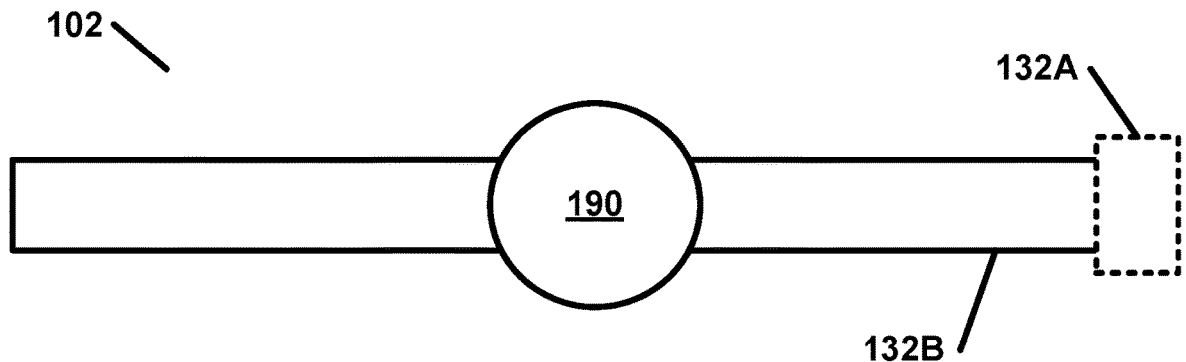

FIG. 1C illustrates an example of a tourniquet as per an aspect of various embodiments. Tourniquet 102 may comprise an actuator 190. The tourniquet 102 may comprise at least one adjustable component (e.g. 132A and/or 132B). The at least one adjustable component (e.g. 132A and/or 132B) may be distinct from actuator 190. Actuator 190 may be configured to activate at least one of the at least one adjustable component (e.g. 132B).

According to an embodiment, a spring-activated tourniquet may be configured to occlude blood flow in at least one artery of a wearer. The spring-activated tourniquet may comprise a compression spring. The compression spring may surround at least a portion of a flexible member configured to operate around a portion of a wearer. The flexible member may, for example, comprise a strap, a cable, a cord, combinations thereof, and/or the like. The flexible member may comprise at least one adjustable component. The spring-activated tourniquet may comprise a spring housing. The spring housing may surround at least a portion of the flexible member. The spring housing may be coupled to a first end of the compression spring at a first end of the spring housing. The spring-activated tourniquet may comprise a release mechanism. The release mechanism may be coupled to a second end of the spring housing. The release mechanism may be configured to contain the compression spring in a compressed state when the release mechanism is coupled to the second end of the spring housing. The release mechanism may comprise, for example, a hair pin, a cotter pin, a reusable cotter pin, a hitch pin, a cotterless hitch pin, a clevis pin, a spring loaded pin, a safety pin, a mechanical switch, a thumb screw, a key, combinations thereof, and/or the like. A first end of the flexible member may be coupled to the first end of the spring housing and/or the first end of the compression spring. The second end of the flexible member may be coupled to the second end of the compression spring. The compression spring may be configured to cause a pressure within a range of 6-8 PSI to be exerted on the wearer when the compression spring is released from the spring housing. The compression spring may be released from the spring housing when the release mechanism is removed from the second end of the spring housing. At least one spring-activated tourniquet may be embedded into a suit configured to be worn by a wearer. Each of the at least one spring-activated tourniquet may be activated by an independent release mechanism. Independent release mechanism(s) may be coupled to a rip cord, a loop, a handle, combinations thereof, and/or the like.

Figure 2A:
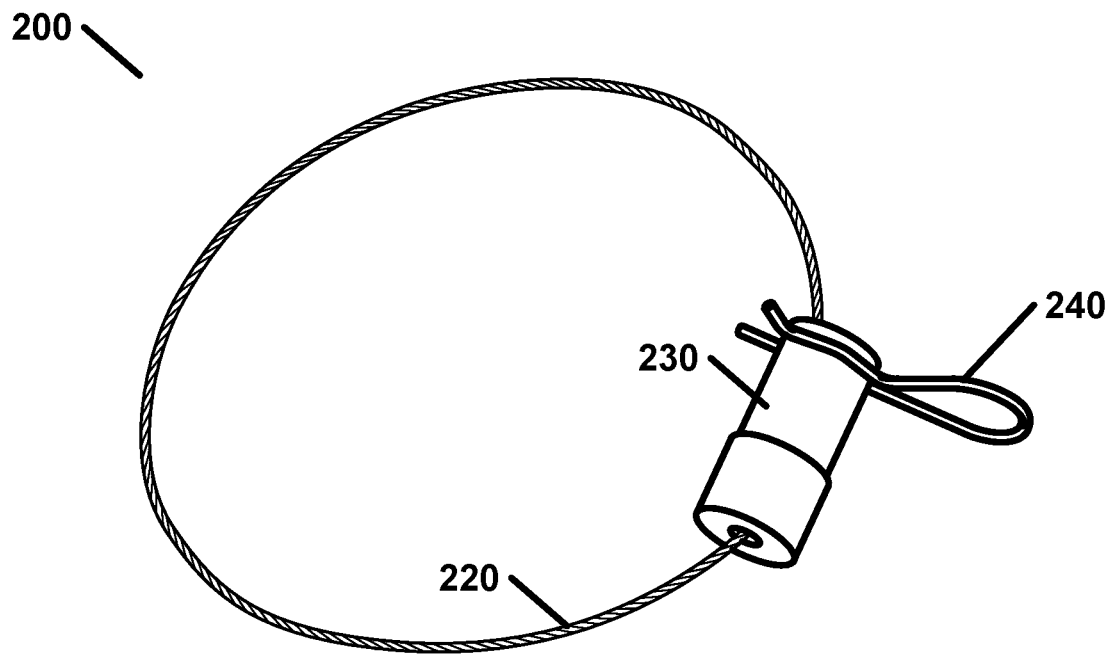
FIG. 2A illustrates an example of a tourniquet as per an aspect of an embodiment.

FIG. 2A illustrates an example of a tourniquet as per an aspect of an embodiment. Spring-activated tourniquet 200 may comprise a compression spring. The compression spring may be compressed into spring housing 230. The compression spring may surround at least a portion of flexible member 220. In a compressed state, the compression spring may be retained by release mechanism 240.

Figure 2B:
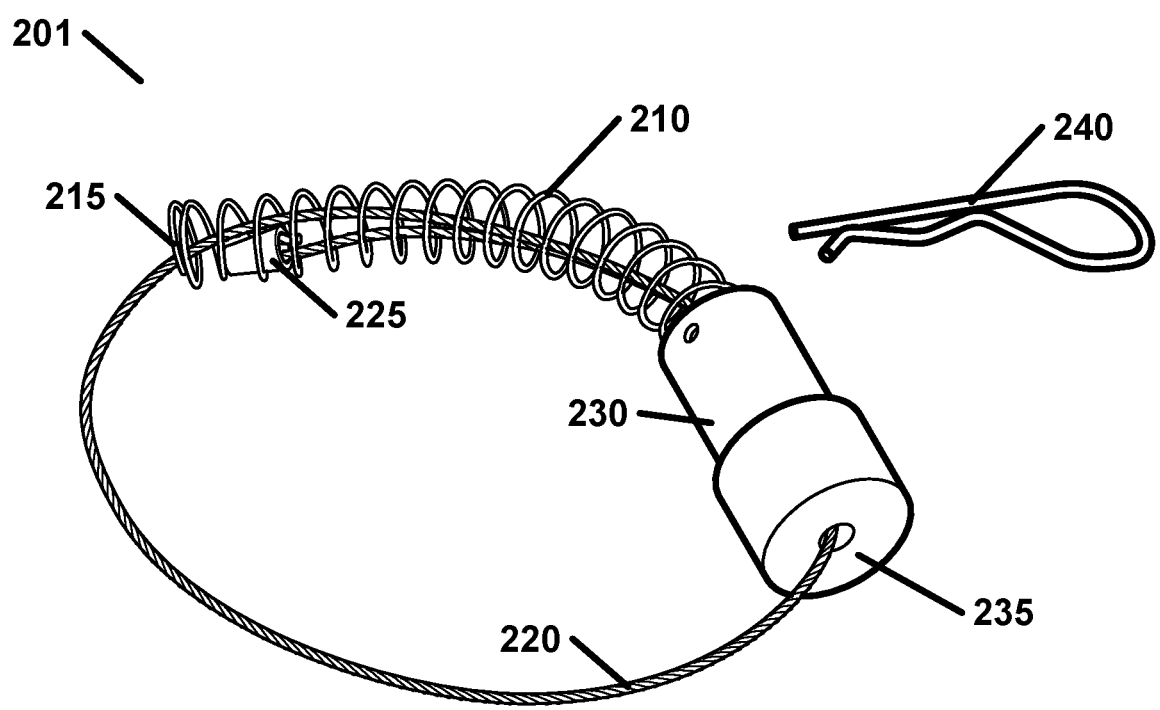
FIG. 2B illustrates an example of an activated tourniquet as per an aspect of an embodiment.

FIG. 2B illustrates an example of an activated tourniquet as per an aspect of an embodiment. Activated tourniquet 201 may comprise compression spring 210. Compression spring 210 may surround at least a portion of flexible member 220. In a decompressed state, a first end of compression spring 210 may be disposed to a first end 235 of spring housing 230. Removal of release mechanism 240 from a second end of the spring housing 230 may cause compression spring 210 to decompress. A second end 215 of the compression spring 210 may be coupled to a second end 225 of the flexible member 220.

Figure 3:
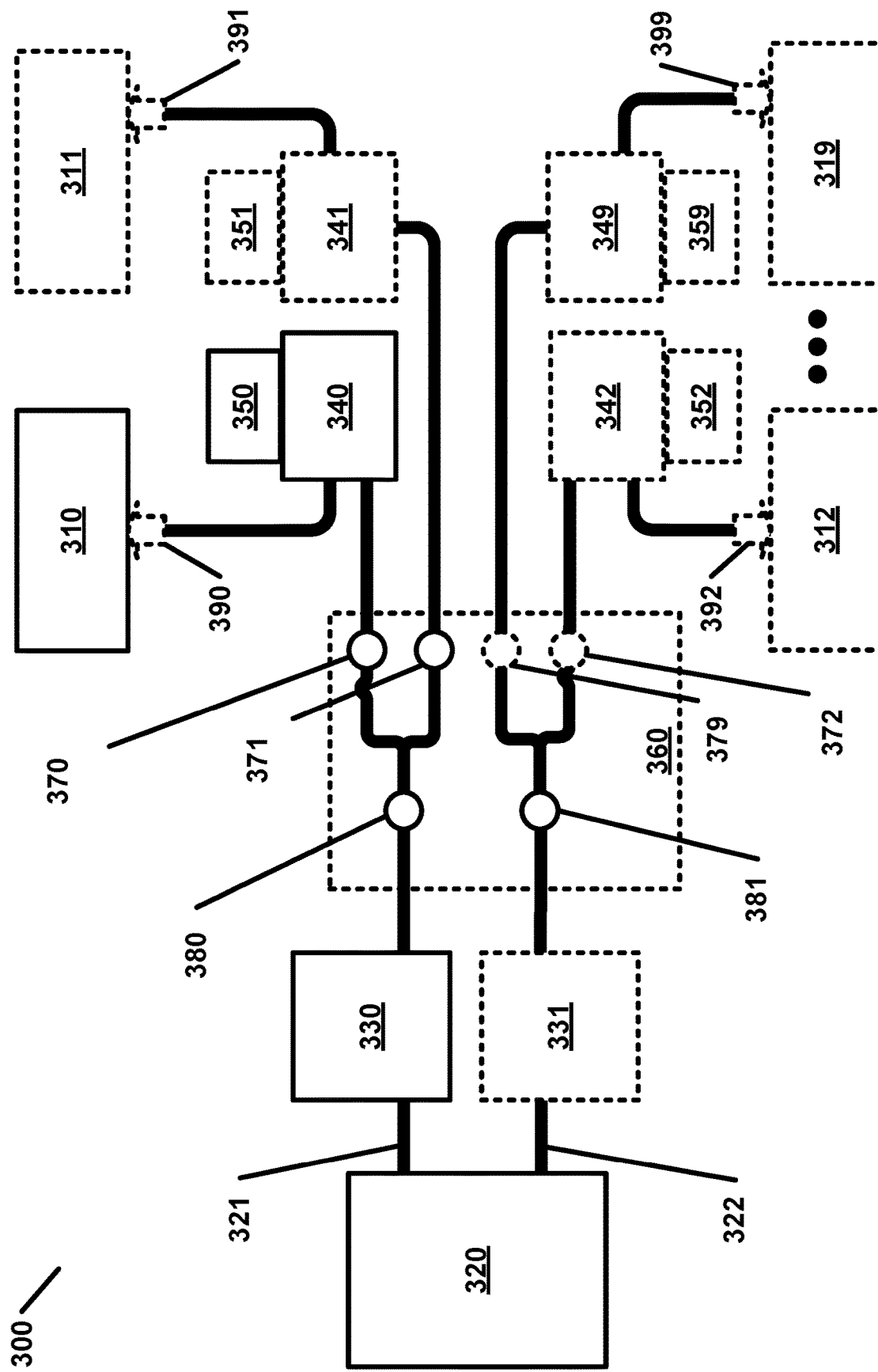
FIG. 3 is a block diagram showing a wearable emergency hemorrhage cessation system as per an aspect of various embodiments.

FIG. 3 is a block diagram showing a wearable emergency hemorrhage cessation system as per an aspect of various embodiments. The wearable emergency hemorrhage cessation system 300 may comprise at least one tourniquet (e.g. 310, 311, 312 . . . 319). Each of the at least one tourniquet (e.g. 310, 311, 312 . . . 319) may be in fluid communication with one of at least one check valve (e.g. 390, 391, 392 . . . 399). The wearable emergency hemorrhage cessation system 300 may comprise at least one compressed gas source 320, at least one fixed pressure regulator (e.g. 330 and 331), at least one valve (e.g. 340, 341, 342 . . . 349), and at least one switch (e.g. 350, 351, 352 . . . 359). The at least one compressed gas source 320 may be in fluid communication with the at least one fixed pressure regulator (e.g. 330 and 331) through employment of at least one fluid conduit (e.g. 321 and 322). The at least one fixed pressure regulator (e.g. 330 and 331) may be in fluid communication with the at least one valve (e.g. 340, 341, 342 . . . 349). The wearable emergency hemorrhage cessation system 300 may comprise a manifold 360. The manifold 360 may comprise a plurality of ports (e.g. 370, 371, 372 . . . 379, 380, and 381). The manifold 360 may be configured to couple a plurality of output ports (e.g. 370 and 371) with an input port (e.g. 380). The manifold 360 may, for example, be configured to cause fluid communication between one (e.g. 330) of the at least one fixed pressure regulator and two (e.g. 340 and 341) of the at least one valve. Each of the at least one valve (e.g. 340, 341, 342 . . . 349) may be coupled to one of at least one switch (e.g. 350, 351, 352 . . . 359). Embodiments of the wearable emergency hemorrhage cessation system 300 may be void of electrical components.

Figure 4:
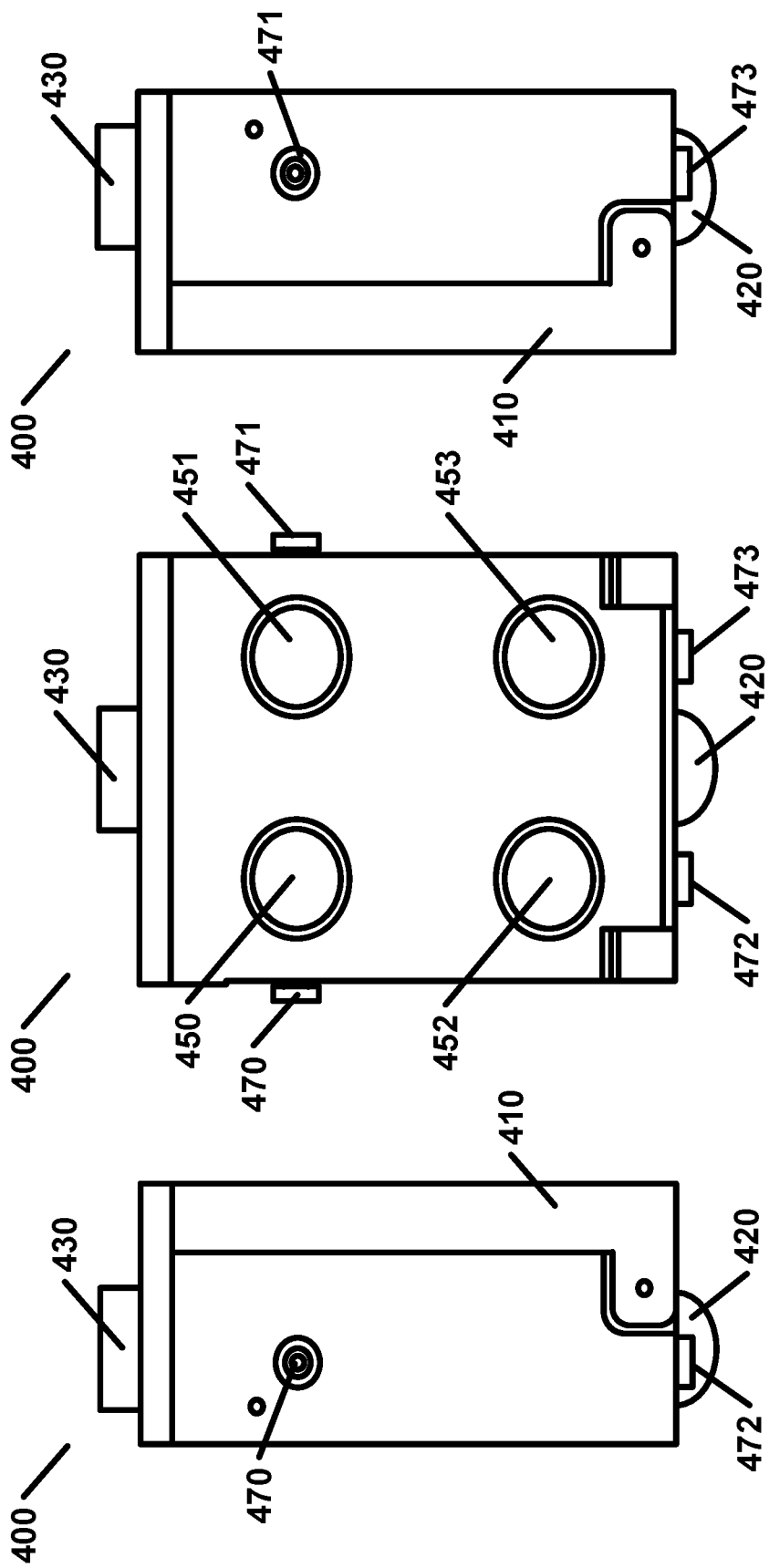
FIG. 4A, FIG. 4B, and FIG. 4C illustrate views of an example control unit as per an aspect of an embodiment.

FIG. 4A, FIG. 4B and FIG. 4C illustrate example views of a control unit 400 as per an aspect of an embodiment. A right (from a wearer's perspective) side view (FIG. 4A) illustrates the right side of a control unit 400. A front view (FIG. 4B) illustrates the front view of the control unit without cover 410. The control unit 400 may comprise compressed gas source 420, fixed pressure regulator 430, upper right fluid conduit port 470, lower right fluid conduit port 472, upper left fluid conduit port 471, lower left fluid conduit port 473, upper right switch 450, lower right switch 452, upper left switch 451, and lower left switch 453. Upper right switch 450 may be configured to activate a valve in fluid communication with upper right fluid conduit port 470. Lower right switch 452 may be configured to activate a valve in fluid communication with lower right fluid conduit port 472. Upper left switch 451 may be configured to activate a valve in fluid communication with upper left fluid conduit port 471. Lower left switch 453 may be configured to activate a valve in fluid communication with lower left fluid conduit port 473. A left side view (FIG. 4C) illustrates the left side of the control unit 400.

Figure 5:
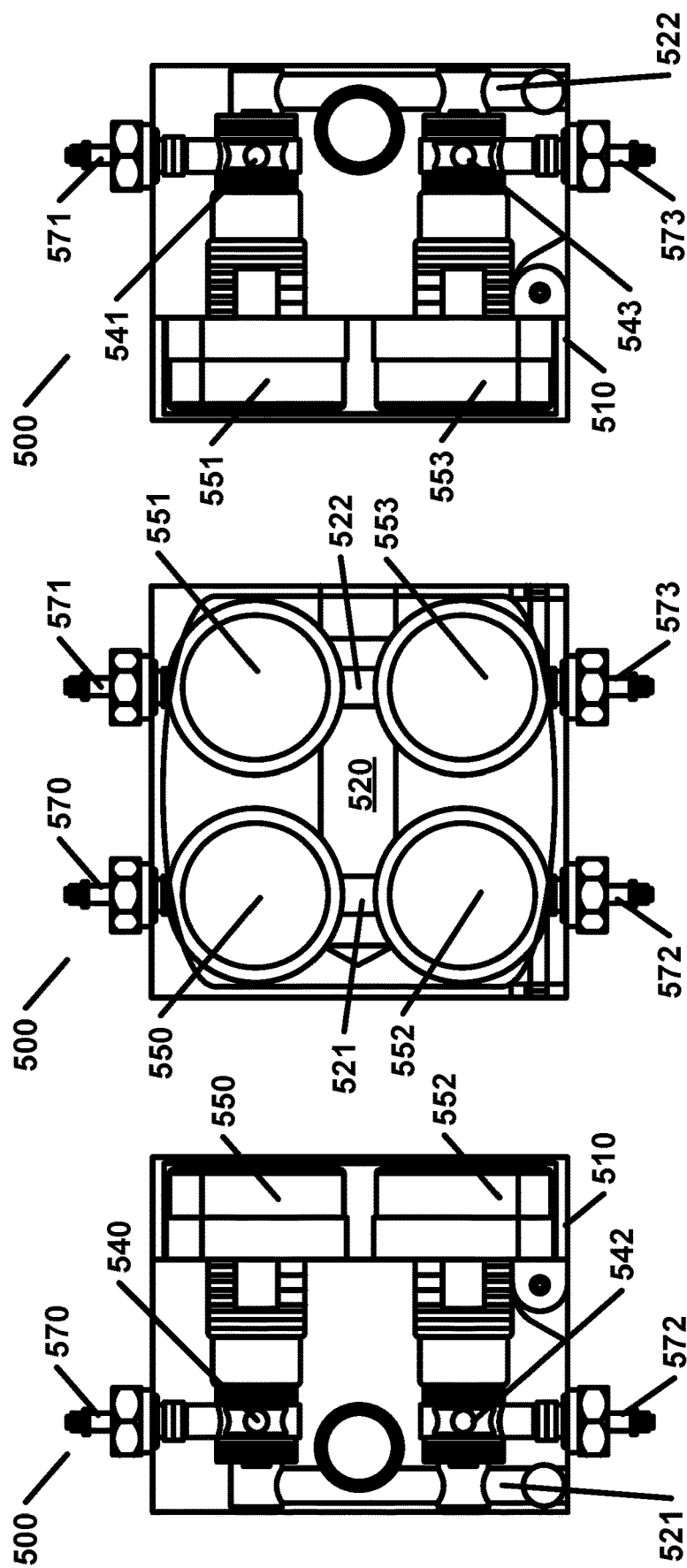
FIG. 5A, FIG. 5B, and FIG. 5C illustrate views of an example control unit as per an aspect of an embodiment.

FIG. 5A, FIG. 5B, and FIG. 5C illustrate example views of a control unit 500 as per an aspect of an embodiment. A right side view (FIG. 5A) illustrates the right side of a control unit 500. Front view (FIG. 5B) illustrates the front view of the control unit 500 without a transparent cover 510. The control unit 500 may comprise compressed gas source 520, upper right fluid conduit port 570, lower right fluid conduit port 572, upper left fluid conduit port 571, lower left fluid conduit port 573, upper right switch 550, lower right switch 552, upper left switch 551, lower left switch 553, upper right valve 540, lower right valve 542, upper left valve 541, lower left valve 543, fluid conduit 521, and fluid conduit 522. Upper right switch 550 may be configured to activate upper right valve 540. Upper right valve 540 may be in fluid communication with upper right fluid conduit port 570. Lower right switch 552 may be configured to activate lower right valve 542. Lower right valve 542 may be in fluid communication with lower right fluid conduit port 572. Upper left switch 551 may be configured to activate upper left valve 541. Upper left valve 541 may be in fluid communication with upper left fluid conduit port 571. Lower left switch 553 may be configured to activate lower left valve 543. Lower left valve 543 may be in fluid communication with lower left fluid conduit port 573. Fluid conduit 521 may be in fluid communication with compressed gas source 520 and at least one valve (e.g. 550 and 552). Fluid conduit 522 may be in fluid communication with compressed gas source 520 and at least one valve (e.g. 551 and 553). A left side view (FIG. 5C) illustrates the left side of the control unit 500.

According to some of the various embodiments, a control unit may comprise at least one manifold. A wearable system may comprise a control unit configured for fluid communication with, for example, two to thirteen tourniquets. The wearable system may, for example, comprise two control units. Each of the two control units may, for example, be configured as in the previous example and may be configured for redundancy. Each of the two control units may, for example, be configured for fluid communication with a distinct compressed gas source. In another embodiment, a first of two control units may be configured for fluid communication with tourniquets employed around the arms of a wearer. A second of two control units may, for example, be configured for fluid communication with tourniquets employed around the legs of a wearer. In yet another embodiment, a first of two control units may be configured for fluid communication with up to 8 tourniquets employed around the appendages of a wearer. A second of two control units may, for example, be configured for fluid communication with up to 5 junctional tourniquets. In yet another embodiment, the wearable system may comprise a plurality of control units, each configured for fluid communications with one tourniquet. A control unit may comprise a ballistic and fragmentation resistant housing. A control unit may comprise a cover configured to prevent accidental activation of switches coupled to the control unit. The cover may be hinged. The cover may comprise a transparent material.

Figure 6:
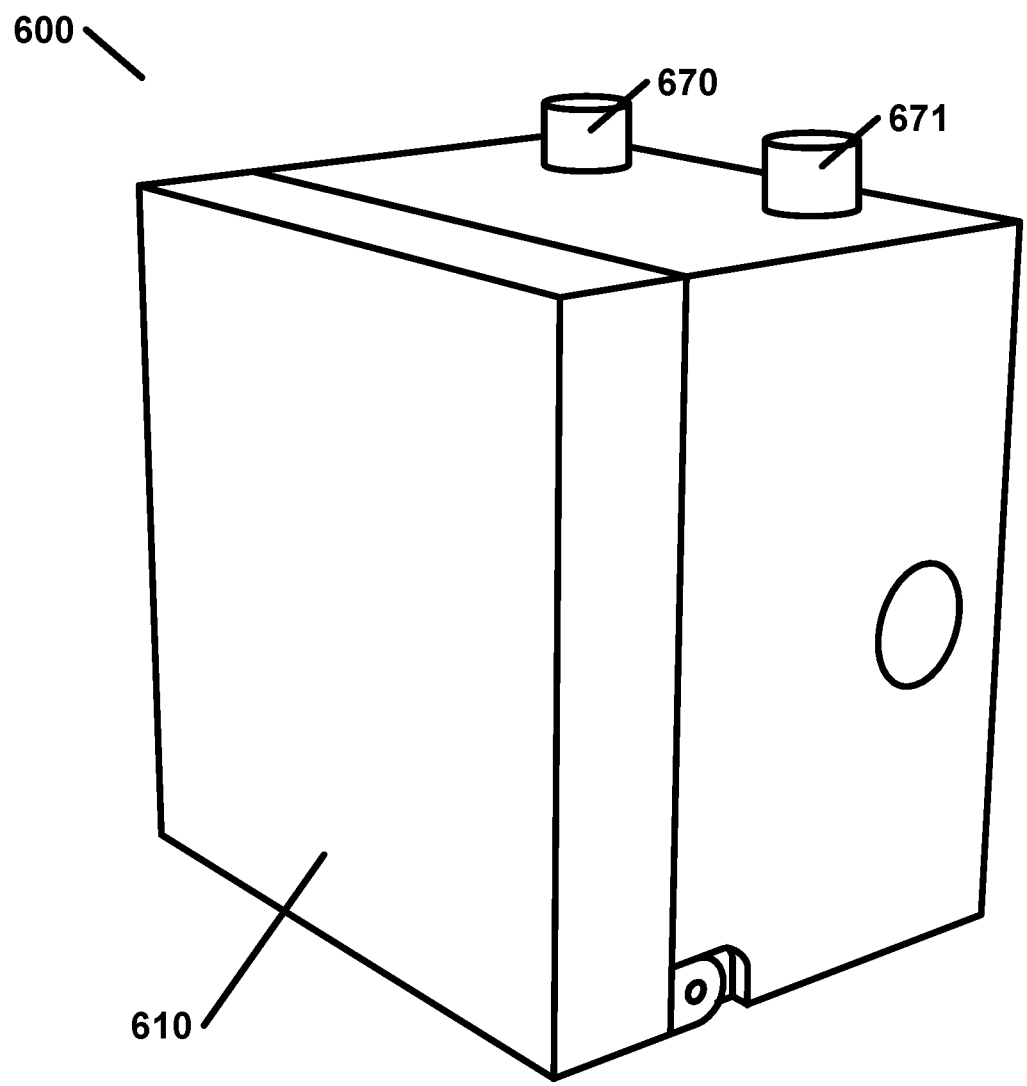
FIG. 6 illustrates an example exterior of a control unit as per an aspect of an embodiment.

FIG. 6 illustrates an example exterior of a control unit as per an aspect of an embodiment. Control unit 600 may comprise upper right fluid conduit port 670, upper left fluid conduit port 671, and opaque cover 610.

Figure 7:
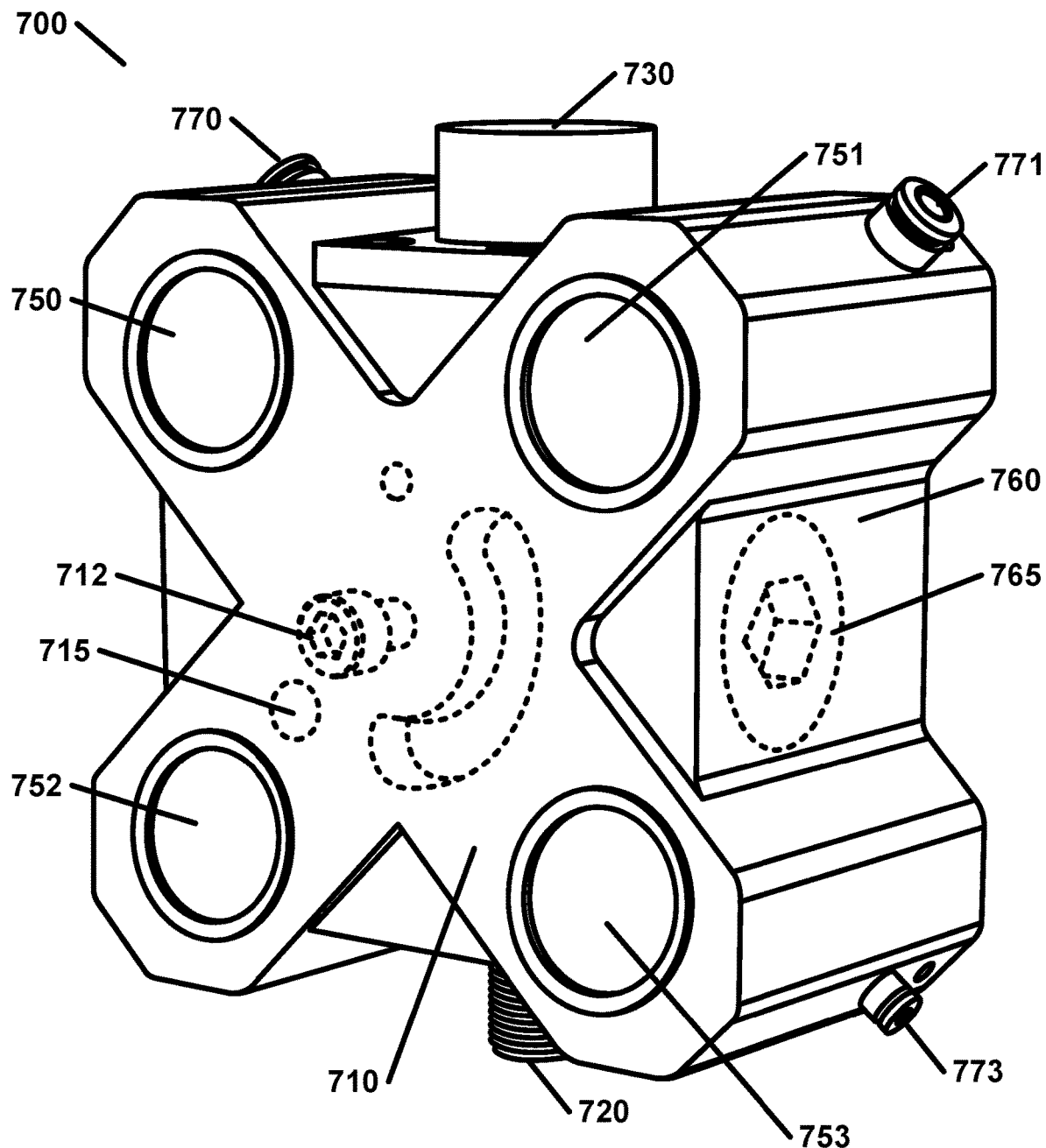
FIG. 7 illustrates an example of a control unit as per an aspect of various embodiments.

FIG. 7 illustrates an example of a control unit as per an aspect of various embodiments. A control unit 700 may comprise at least one switch (e.g. 750, 751, 752, and 753), at least one valve, and at least one fixed pressure regulator (e.g. 730). The control unit 700 may comprise at least one manifold (e.g. 760). Manufacture of the at least one manifold (e.g. 760) may require at least one manifold plug (e.g. 765). The control unit 700 may be configured to accept a cover (not shown) configured to rotate. The cover may be secured to the control unit through employment of a cover screw 712. The cover may comprise a rotation pin configured for travel in a rotation slot 717. The rotation slot 717 may be configured to limit rotation of the cover. The control unit 700 may comprise a retaining pin hole 715 or slot configured to accept a retaining pin. The retaining pin may be configured to prevent rotation of the cover until removed. The at least one manifold (e.g. 760) may comprise at least one pneumatic fitting (e.g. 720). The at least one pneumatic fitting (e.g. 720) may be configured to accept at least one compressed gas. The at least one manifold (e.g. 760) may be filled with compressed gas to a pressure on the order of, for example, 850 PSI. The at least one pneumatic fitting (e.g. 720) may be configured to connect to at least one compressed gas source. The at least one manifold (e.g. 760) may be in fluid communication with at least one fluid conduit port (e.g. 770, 771, and 773).

Figure 8A:
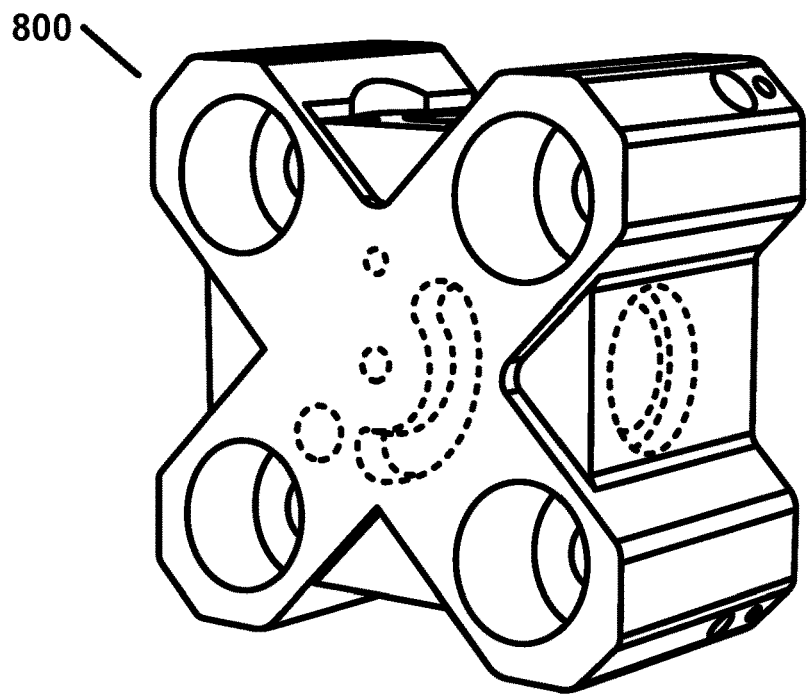
FIG. 8A illustrates an example of a manifold as per an aspect of various embodiments.
Figure 8B:
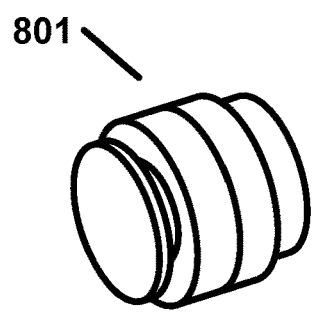
FIG. 8B illustrates an example of a switch as per an aspect of an embodiment.
Figure 8C:
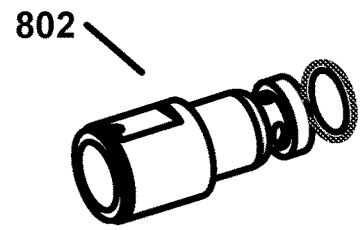
FIG. 8C illustrates an example of a valve as per an aspect of an embodiment.
Figure 8D:
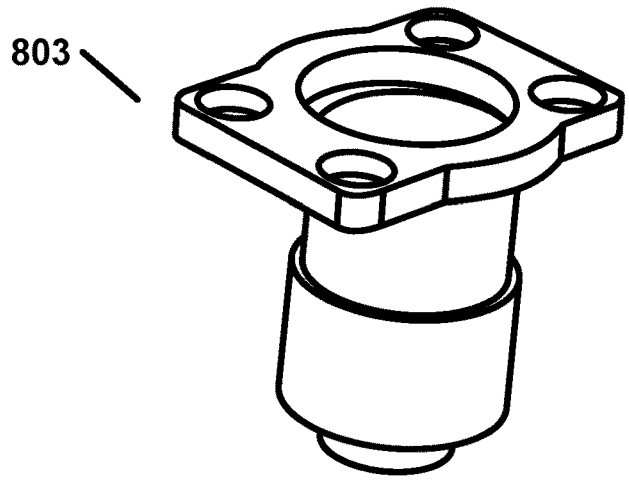
FIG. 8D illustrates an example of a pressure regulator as per an aspect of an embodiment.

FIG. 8A illustrates an example of a manifold 800 as per an aspect of various embodiments. FIG. 8B illustrates an example of a switch 801 as per an aspect of an embodiment. FIG. 8C illustrates an example of a valve 802 as per an aspect of an embodiment. FIG. 8D illustrates an example of a pressure regulator 803 as per an aspect of an embodiment.

Figure 9:
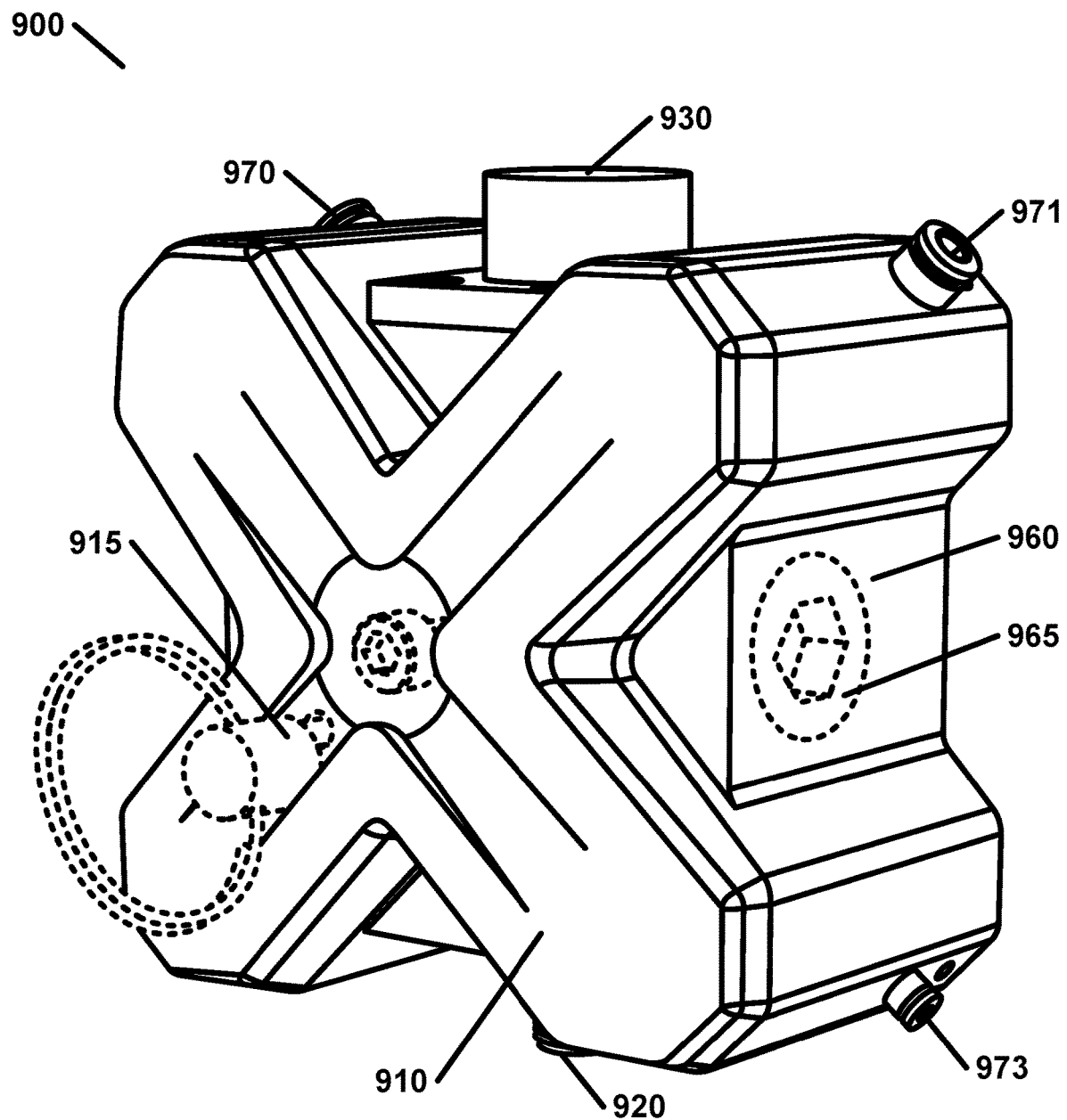
FIG. 9 illustrates an example exterior of a control unit as per an aspect of various embodiments.

FIG. 9 illustrates an example exterior of a control unit as per an aspect of various embodiments. A control unit 900 may comprise at least one switch, at least one valve, at least one fixed pressure regulator (e.g. 930), and at least one cover (e.g. 910). The control unit 900 may comprise at least one manifold (e.g. 960) and at least one manifold plug (e.g. 965). The at least one cover (e.g. 910) may be rotatable. Rotation of at least one cover (e.g. 910) may be spring-activated. Rotation of at least one cover (e.g. 910) may be prevented through employment of at least one retaining pin (e.g. 915). The at least one cover (e.g. 910) may take the shape of, for example, an X, a star, a circle, combinations thereof, and/or the like. For example, removing one of the at least one retaining pin (e.g. 915) may cause one of the at least one cover (e.g. 910) to rotate left by 45 degrees to expose up to four switches. The at least one manifold (e.g. 960) may comprise at least one pneumatic fitting (e.g. 920). The at least one manifold (e.g. 960) may be in fluid communication with at least one fluid conduit port (e.g. 970, 971, and 973).

Figure 10:
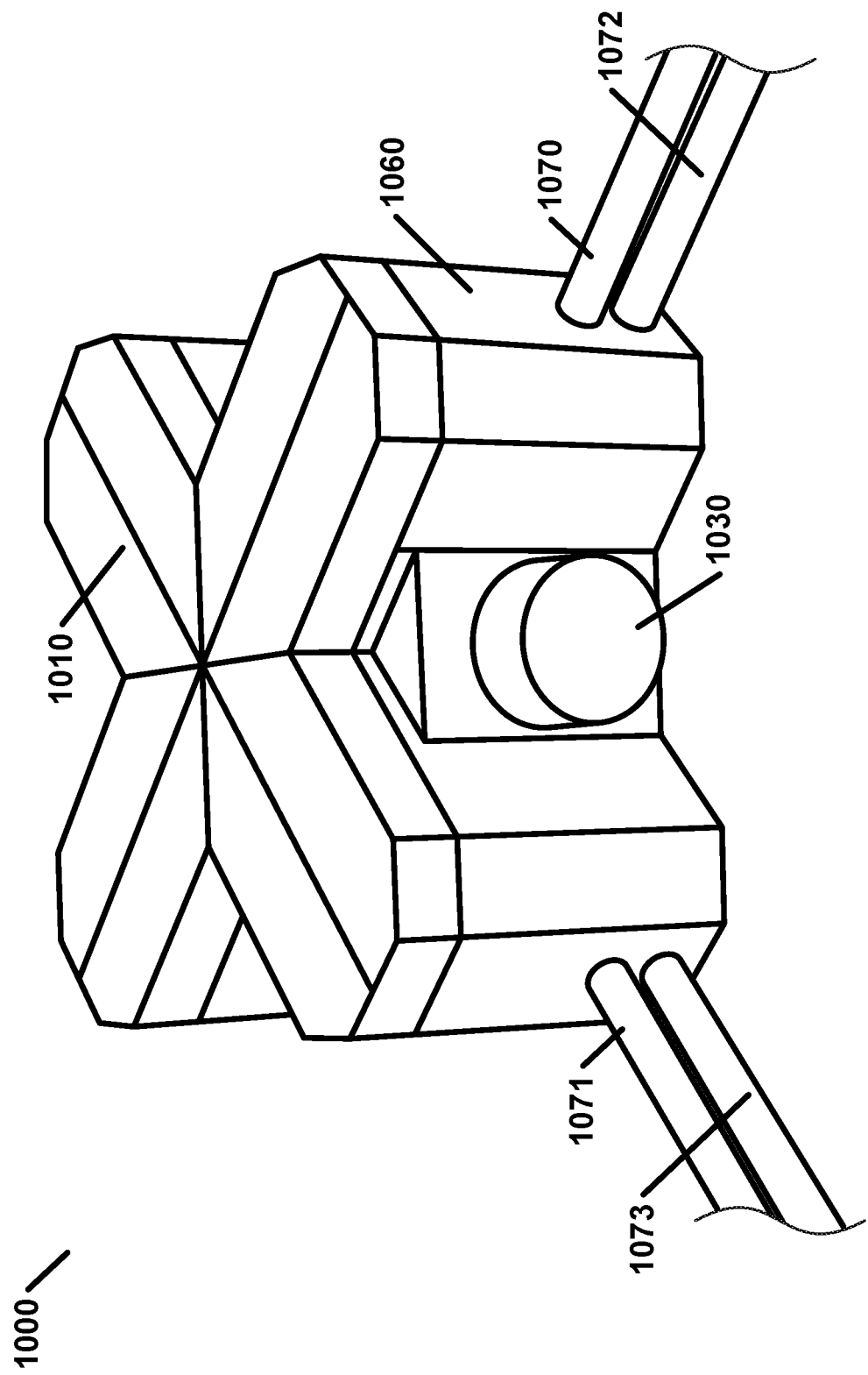
FIG. 10 illustrates an example exterior of a control unit as per an aspect of an embodiment.

FIG. 10 illustrates an example exterior of a control unit as per an aspect of an embodiment. A control unit 1000 may comprise a cover 1010 and a manifold 1060. The manifold 1060 may be in fluid communication with upper right fluid conduit 1070, lower right fluid conduit 1072, upper left fluid conduit 1071, and lower left fluid conduit 1073. A plurality of fluid conduits (e.g. 1070, 1071, 1072, and 1073) may be in fluid communication with fluid conduit ports along one side (e.g. the top) of manifold 1060. Fluid conduit ports along one side of manifold 1060 may facilitate more protection to at least one of the plurality of fluid conduits (e.g. 1070, 1071, 1072, and 1073). For example, body armor, a suit, or a vest may comprise a frame or chassis. An example of body armor with a frame includes the XFrame™ by Tyr Tactical® of Peoria, Ariz. An example of body armor comprising a chassis includes CAGE Armor Chassis™ by Crye Precision™ of Brooklyn, N.Y. In these examples, fluid conduits for the lower body of a wearer may be routed over the shoulders of the frame or chassis. The frame may cross in the back. In this example, the lower left fluid conduit may be in fluid communication with a tourniquet on the lower right side of a wearer's body. Therefore, in this example, a lower right switch may be configured to activate a lower right valve in fluid communication with the lower left fluid conduit port. Similarly, a lower left switch may be configured to activate a lower left valve in fluid communication with the lower right fluid conduit port. At least one of a plurality of fluid conduits (e.g. 1070, 1071, 1072, and 1073) may be in fluid communication with one of at least one pressure regulator (e.g. 1030).

Figure 11B:
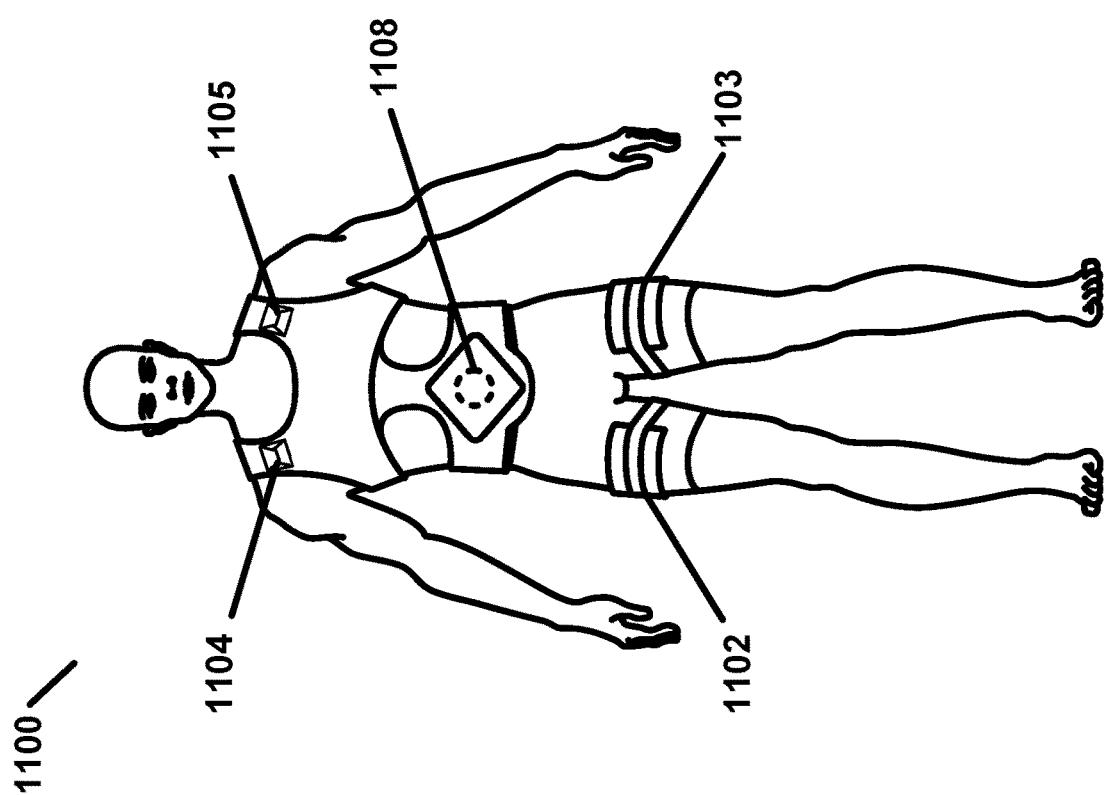
FIGS. 11A and 11B illustrate examples of a plurality of tourniquets according to various aspects of various embodiments.
Figure 11A:
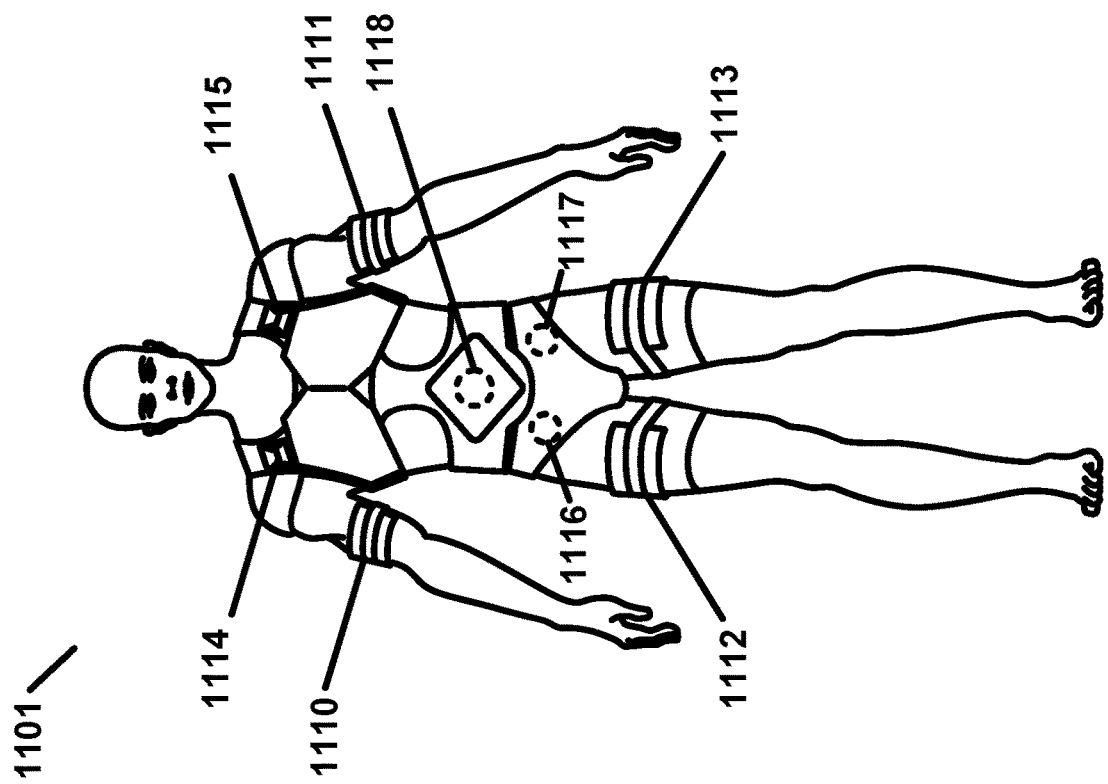

FIG. 11A illustrates an example of a plurality of tourniquets according to an aspect of various embodiments. A wearable emergency hemorrhage cessation system 1100 may comprise a plurality of tourniquets (e.g. 1102, 1103, 1104, 1105, and 1108). At least some of the plurality of tourniquets may be configured to operate as junctional tourniquets (e.g. 1104, 1105, and 1108).

FIG. 11B illustrates an example of a plurality of tourniquets according to an aspect of various embodiments. A wearable emergency hemorrhage cessation system 1101 may comprise a plurality of tourniquets (e.g. 1110, 1111, 1112, 1113, 1114, 1115, 1116, 1117, and 1118). At least some of the plurality of tourniquets may be configured to operate as junctional tourniquets (e.g. 1114, 1115, 1116, 1117, and 1118).

Figure 12:
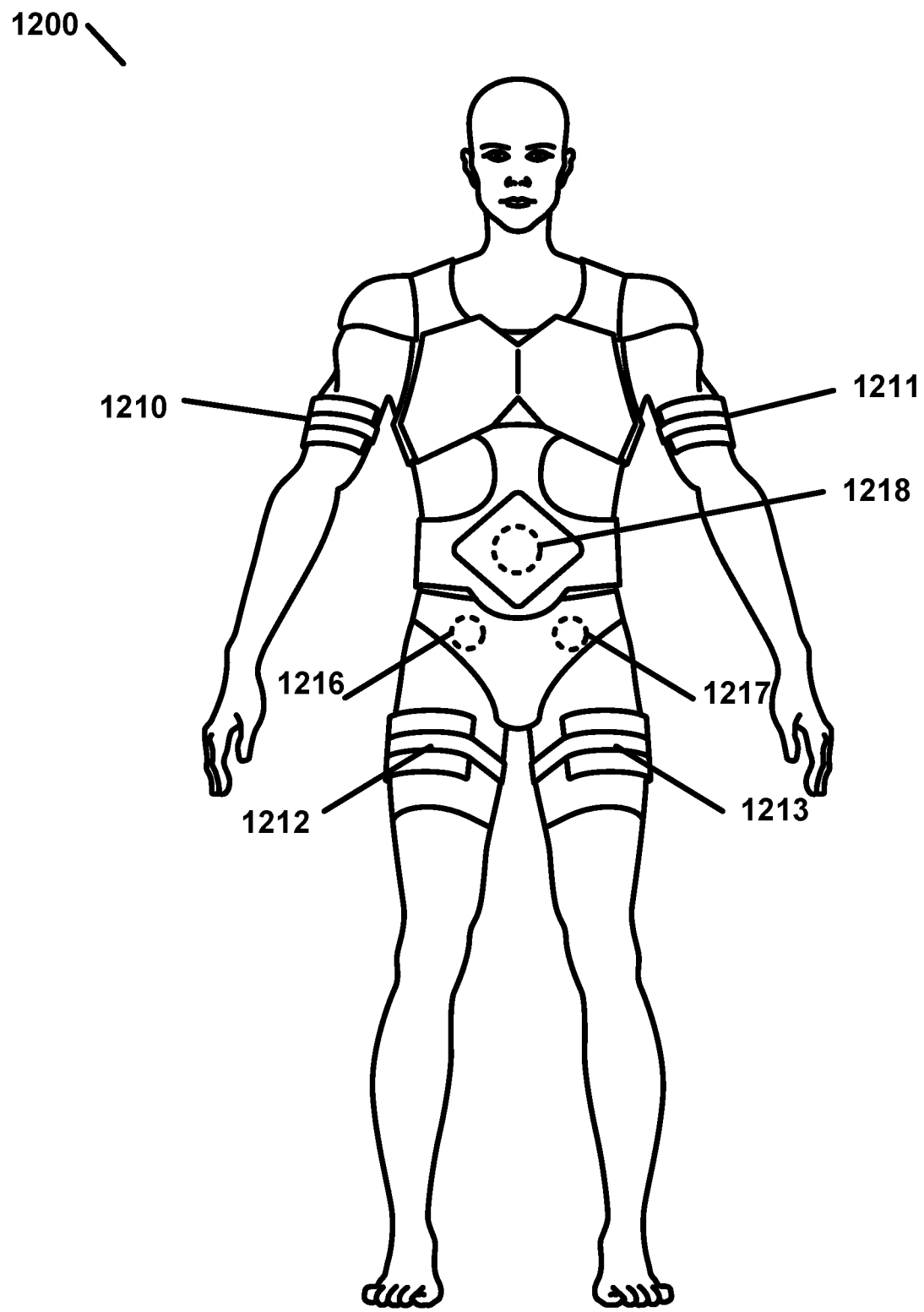
FIG. 12 illustrates an example of a plurality of tourniquets according to an aspect of various embodiments.

FIG. 12 illustrates an example of a plurality of tourniquets according to an aspect of various embodiments. A wearable emergency hemorrhage cessation system 1200 may comprise a plurality of tourniquets (e.g. 1210, 1211, 1212, 1213, 1216, 1217, and 1218). At least some of the plurality of tourniquets may be configured to operate as junctional tourniquets (e.g. 1216, 1217, and 1218).

Figure 13:
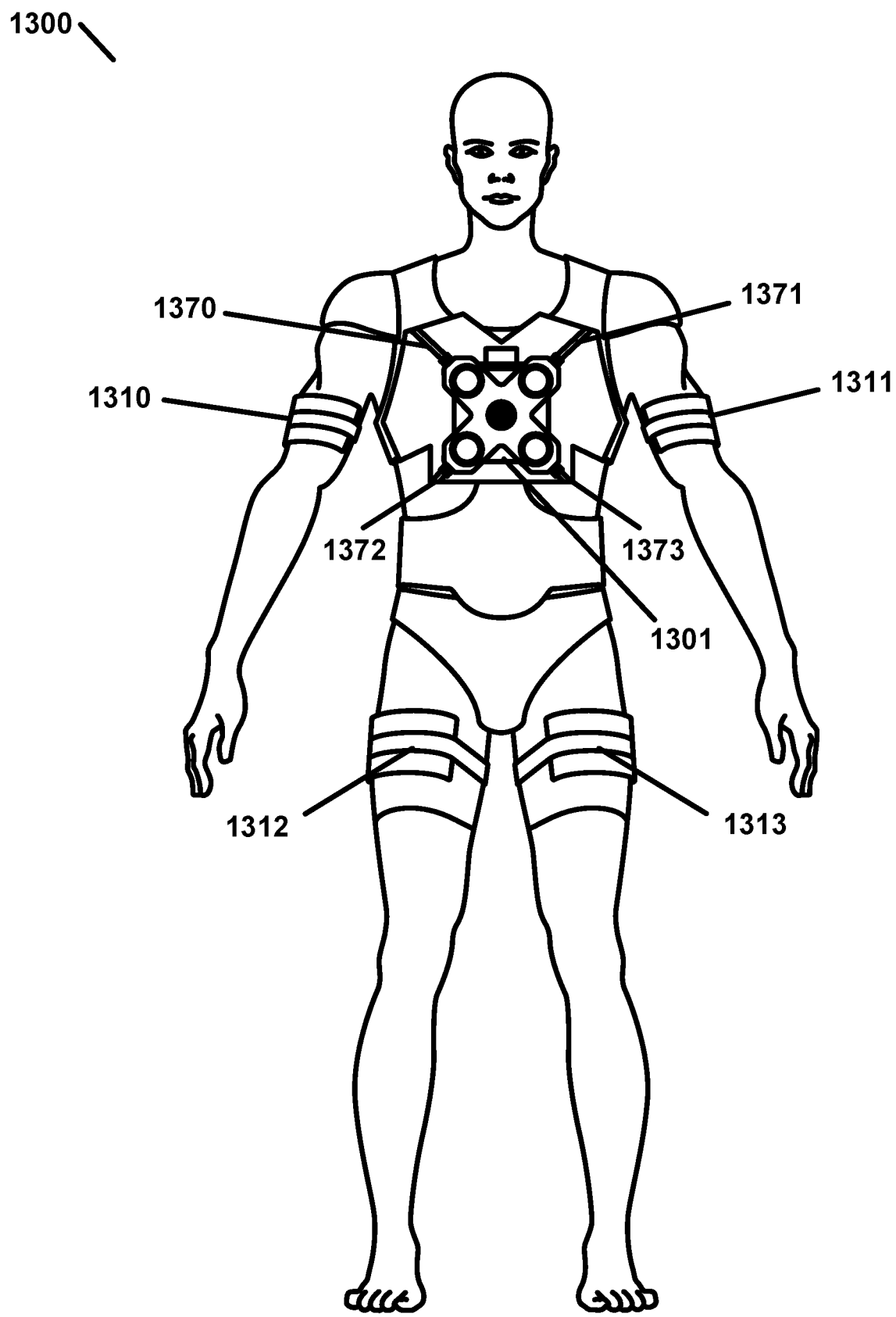
FIG. 13 illustrates an example of a plurality of tourniquets in communication with an example control unit according to an aspect of various embodiments.

FIG. 13 illustrates an example of a plurality of tourniquets in communication with an example control unit according to an aspect of various embodiments. A wearable emergency hemorrhage cessation system 1300 may comprise a plurality of tourniquets (e.g. 1310, 1311, 1312, and 1313), a plurality of fluid conduits (e.g. 1370, 1371, 1372, and 1373), and a control unit 1301.

Figure 14:
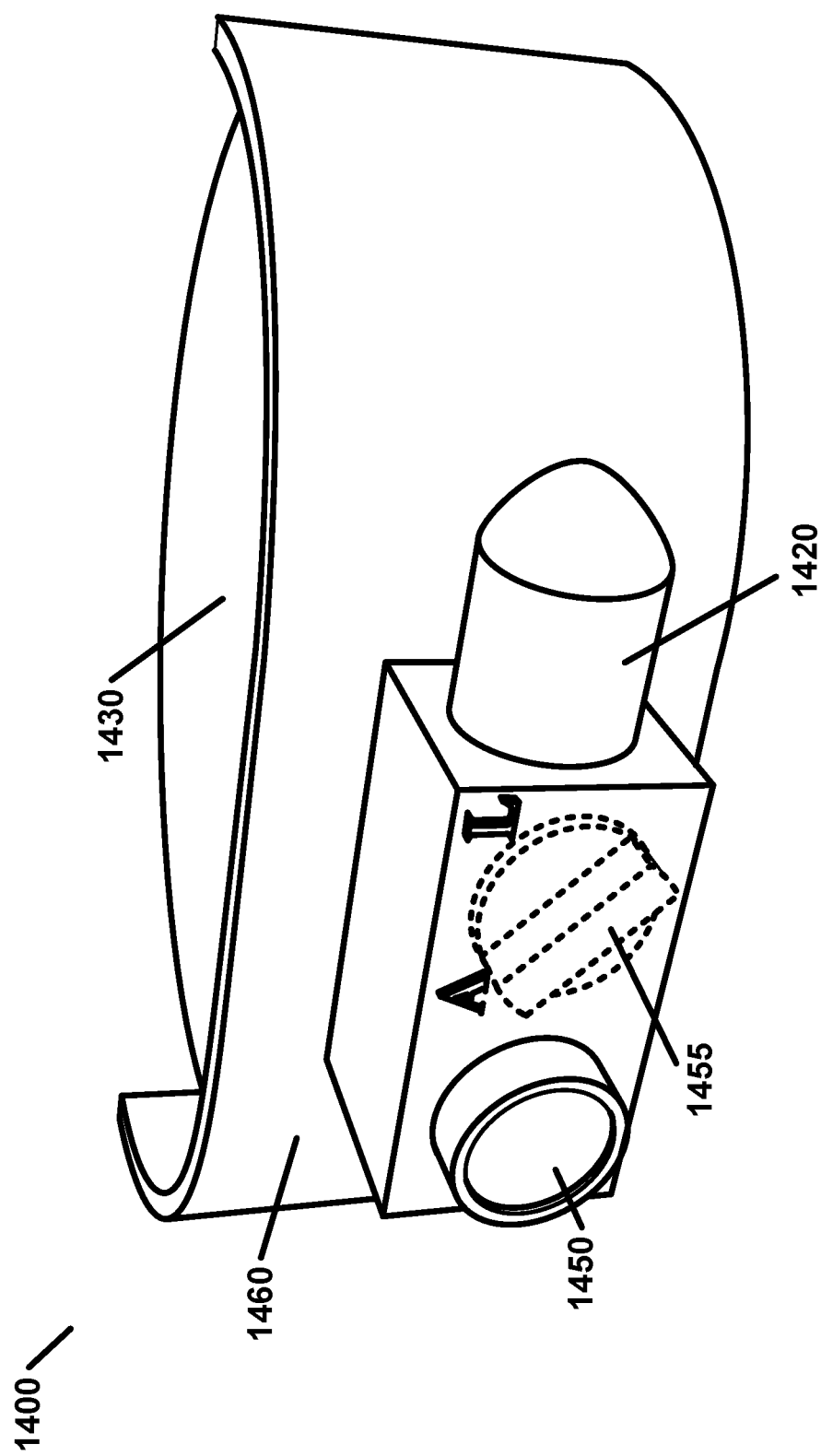
FIG. 14 illustrates an example of a wearable emergency hemorrhage cessation system as per an aspect of an embodiment.

FIG. 14 illustrates an example of a wearable emergency hemorrhage cessation system as per an aspect of an embodiment. The wearable emergency hemorrhage cessation system 1400 may comprise a tourniquet. The tourniquet may comprise an inflatable chamber, a sleeve 1460, and at least one adjustable component 1430. The wearable emergency hemorrhage cessation system 1400 may comprise a switch 1450, a valve, a compressed gas source 1420, and at least one fixed pressure regulator. The wearable emergency hemorrhage cessation system 1400 may comprise a selector switch 1455. The selector switch 1455 may be configured to cause selection of one of at least two fixed pressure regulators. The compressed gas source 1420 may comprise a gas cartridge. The wearable emergency hemorrhage cessation system 1400 may comprise a manifold. The manifold may comprise at least one chamber. At least one of the at least one chamber may be pressurized with at least one compressed gas. Therefore, the pressurized manifold may comprise at least one compressed gas source. Each of the at least two fixed pressure regulators may be configured for a distinct fixed pressure. For example, the selector switch 1455 may comprise two positions. One of the two positions may be configured for an arm of the wearer. One of the two positions may be configured for a leg of the wearer. One of the at least two pressure regulators may be configured for a fixed pressure for an arm of the wearer. One of the at least two pressure regulators may be configured for a fixed pressure for a leg of the wearer. In another example, the selector switch 1455 may comprise at least two positions. One of the at least two positions may be configured for an arm or leg of a child wearer. One of the at least two positions may be configured for an arm or leg of an adult wearer. One of the at least two pressure regulators may be configured for a fixed pressure for an arm or leg of the child wearer. One of the at least two pressure regulators may be configured for a fixed pressure for an arm or leg of the adult wearer. In yet another example, the selector switch 1455 may comprise at least two positions. One of the at least two positions may be configured for an arm or leg of the wearer. One of the at least two positions may be configured for a junctional tourniquet of the wearer. One of the at least two pressure regulators may be configured for a fixed pressure for an arm or leg of the wearer. One of the at least two pressure regulators may be configured for a junctional tourniquet for the wearer The wearable emergency hemorrhage cessation system 1400 may be configured to be portable. The wearable emergency hemorrhage cessation system 1400 may be configured to be placed on the wearer after the wearer has suffered a hemorrhage. The wearable emergency hemorrhage cessation system 1400 may be packaged in at least one ballistic and fragmentation resistant material.

Figure 15:
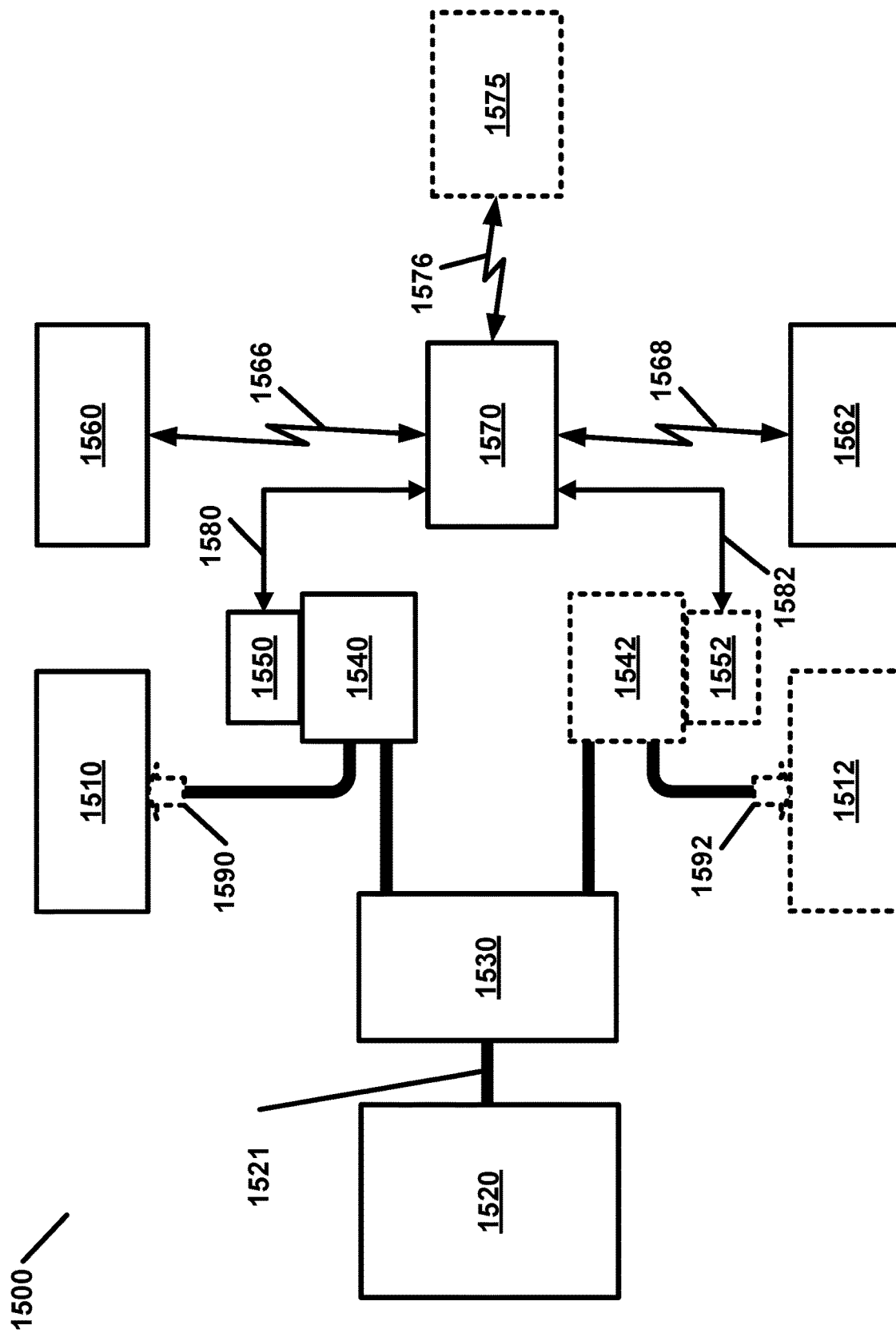
FIG. 15 is a block diagram showing a wearable emergency hemorrhage cessation system as per an aspect of various embodiments.

FIG. 15 is a block diagram showing a wearable emergency hemorrhage cessation system as per an aspect of various embodiments. The wearable emergency hemorrhage cessation system 1500 may comprise at least one tourniquet (e.g. 1510 and 1512). Each of the at least one tourniquet (e.g.

1510 and 1512) may be in fluid communication with one of at least one check valve (e.g. 1590 and 1592). The wearable emergency hemorrhage cessation system 1500 may comprise at least one compressed gas source 1520, at least one fixed pressure regulator 1530, at least one valve (e.g. 1540 and 1542), and at least one switch (e.g. 1550 and 1552). The at least one compressed gas source 1520 may be in fluid communication with the at least one fixed pressure regulator 1530 through employment of at least one fluid conduit 1521. The at least one fixed pressure regulator 1530 may be in fluid communication with the at least one valve (e.g. 1540 and 1542). Each of the at least one valve (e.g. 1540 and 1542) may be coupled to one of the at least one switch (e.g. 1550 and 1552). The wearable emergency hemorrhage cessation system 1500 may comprise at least one physiological sensor (e.g. 1560 and 1562) and a processing unit 1570. The processing unit 1570 may be configured to communicate with the at least one physiological sensor (e.g. 1560 and 1562). At least one communication channel (e.g. 1566 and 1568) may be employed for communication between the processing unit 1570 and the at least one physiological sensor (e.g. 1560 and 1562). The processing unit 1570 may be configured to communicate with the at least one switch (e.g. 1550 and 1552). At least one electrical signal (e.g. 1580 and 1582) may be employed for communication between the processing unit 1570 and the at least one switch (e.g. 1550 and 1552). The processing unit may be configured to communicate with a remote device 1575. At least one communication channel 1576 may be employed for communication between the processing unit 1570 and the remote device 1575. Communication channels may be configured for encrypted communication.

Some of the various embodiments may comprise a method of employing a wearable system. The method may comprise donning the wearable system. The wearable system may be configured to be donned prior to a wearer sustaining an injury. The wearable system may comprise at least one tourniquet. Each of the at least one tourniquet may comprise an inflatable chamber. Each of the at least one tourniquet may be configured to occlude blood flow in at least one artery of a wearer of the wearable system. The wearable system may comprise a fluid conduit in fluid communication with the inflatable chamber. The inflatable chamber may be regulated to a fixed pressure by a fixed pressure regulator. The method may comprise activating a switch. The switch may be activated after a wearer sustains a hemorrhage. The switch may be configured to operate a valve in fluid communication with a compressed gas source and the inflatable chamber.

According to some of the various embodiments, a method of employing a wearable system may comprise adjusting at least one adjustable component. Each of the at least one adjustable component may be associated with one of at least one tourniquet. Each of the at least one adjustable component may be distinct from an inflatable chamber. Each of the at least one adjustable component may comprise a strap, a cable, a cord, a buckle, a clamp, a ring, combinations thereof, and/or the like. The method of employing a wearable system may comprise attaching a compressed gas source to the wearable system. The method of employing a wearable system may comprise receiving, at a processing unit, at least one physiological signal from at least one physiological sensor. The method of employing a wearable system may comprise communicating at least one command from the processing unit to a switch. The at least one command may be based, at least in part, on at least one of the at least one physiological signal. The method of employing a wearable system may comprise activating the switch based, at least in part, on the at least one command.

Figure 16:
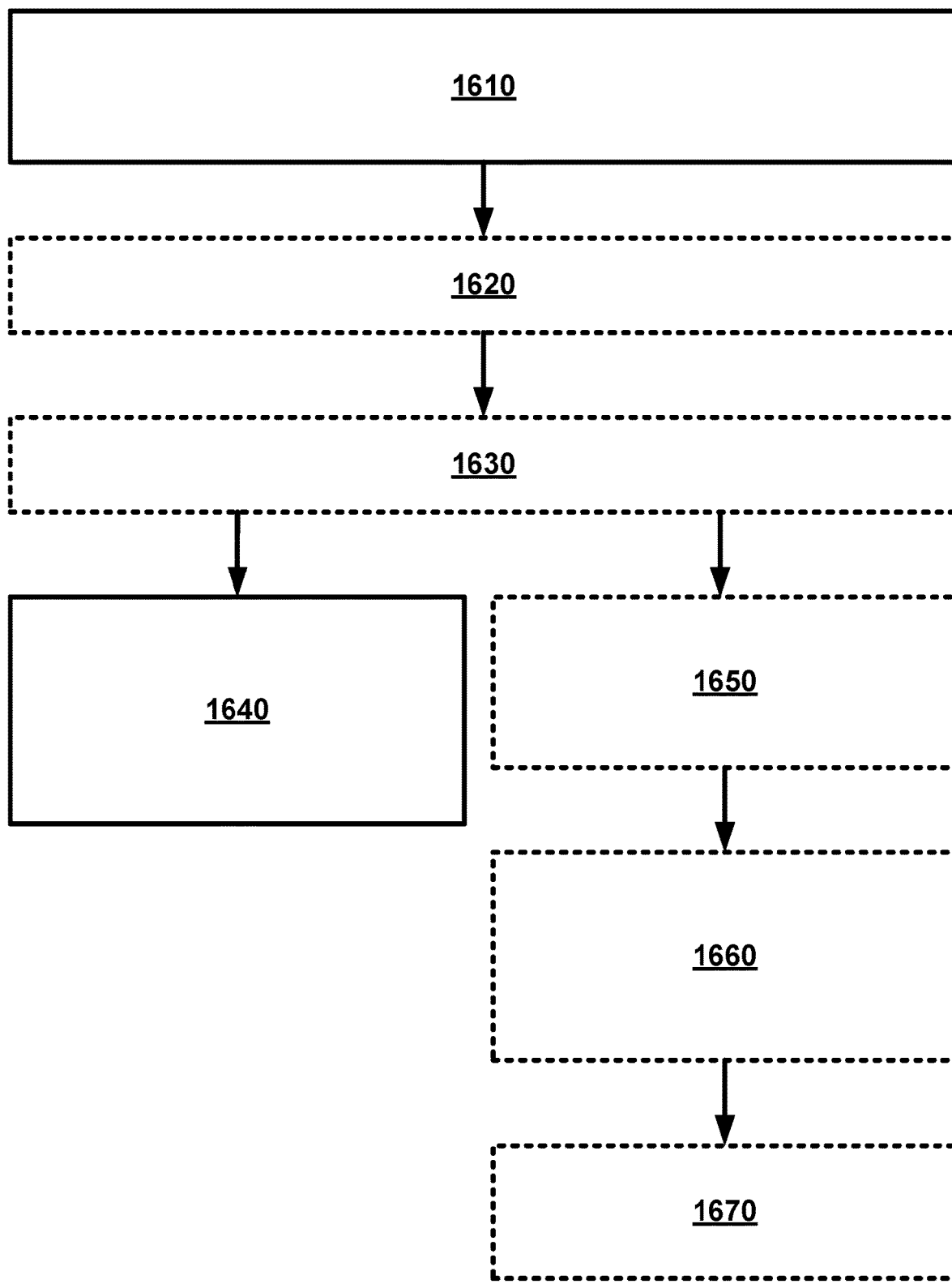
FIG. 16 is an example flow diagram of employing a wearable emergency hemorrhage cessation system as per an aspect of various embodiments.

FIG. 16 is an example flow diagram of employing a wearable emergency hemorrhage cessation system as per an aspect of various embodiments. A wearable system may be donned at 1610. The wearable system may comprise a tourniquet(s) and a fluid conduit(s) in fluid communication with an inflatable chamber(s) regulated to a fixed pressure by a fixed pressure regulator(s). An adjustable component(s) associated with the tourniquet(s) may be adjusted at 1620. A compressed gas source(s) may be attached to the wearable system at 1630. A switch(es) may be activated at 1640. The switch(es) may be configured to operate a valve(s) in fluid communication with the compressed gas source(s) and the inflatable chamber(s). A physiological signal(s) may be received from a physiological sensor(s) at 1650. The physiological signal(s) may be received at a processing unit. A command(s) may be communicated from the processing unit to the switch(es) at 1660. The command(s) may be based, at least in part, on a physiological signal(s). The switch(es) may be activated based, at least in part, on the command(s) at 1670.

According to some of the various embodiments, a wearable system may comprise at least one tourniquet. Each of at least one tourniquet may comprise an actuator. A plurality of tourniquets may share an actuator that may be configured to be engaged and disengaged from each of the plurality of tourniquets. The wearable system may comprise at least one wearable power source. The at least one wearable power source may comprise a battery, a solar cell, a biofuel cell, combinations thereof, and/or the like. The wearable system may comprise at least one switch. Each of the at least one switch may be electrically connected between at least one of the at least one wearable power source, and the actuator of at least one of the at least one tourniquet. Each of the at least one tourniquet may comprise at least one adjustable component distinct from the actuator. The at least one adjustable component may comprise a strap, a cable, a cord, a buckle, a clamp, a ring, combinations thereof, and/or the like. A strap, cable, cord, combinations thereof, and/or the like may be coupled to the actuator.

According to some of the various embodiments, an actuator may comprise a servo motor, a stepper motor, a linear actuator (i.e. actuating along a single plane), a rotary actuator, a solenoid, a pull cord, a pneumatic wrench, combinations thereof, and/or the like. The actuator may be configured to cause a minimum pressure to be exerted to an arm of a wearer, a leg of a wearer, a forearm of a wearer, an upper arm of a wearer, a lower leg of a wearer, an upper leg of a wearer, a shoulder of a wearer, the abdomen of a wearer, a groin of a wearer, combinations thereof, and/or the like. The actuator may be configured to cause a maximum pressure to be exerted to an arm of a wearer, a leg of a wearer, a forearm of a wearer, an upper arm of a wearer, a lower leg of a wearer, an upper leg of a wearer, a shoulder of a wearer, the abdomen of a wearer, a groin of a wearer, combinations thereof, and/or the like. The actuator may be configured to cause a pressure within a range of, for example, 6 to 10 PSI to be exerted on the wearer. The actuator may be removable from at least one of at least one tourniquet.

Figure 17:
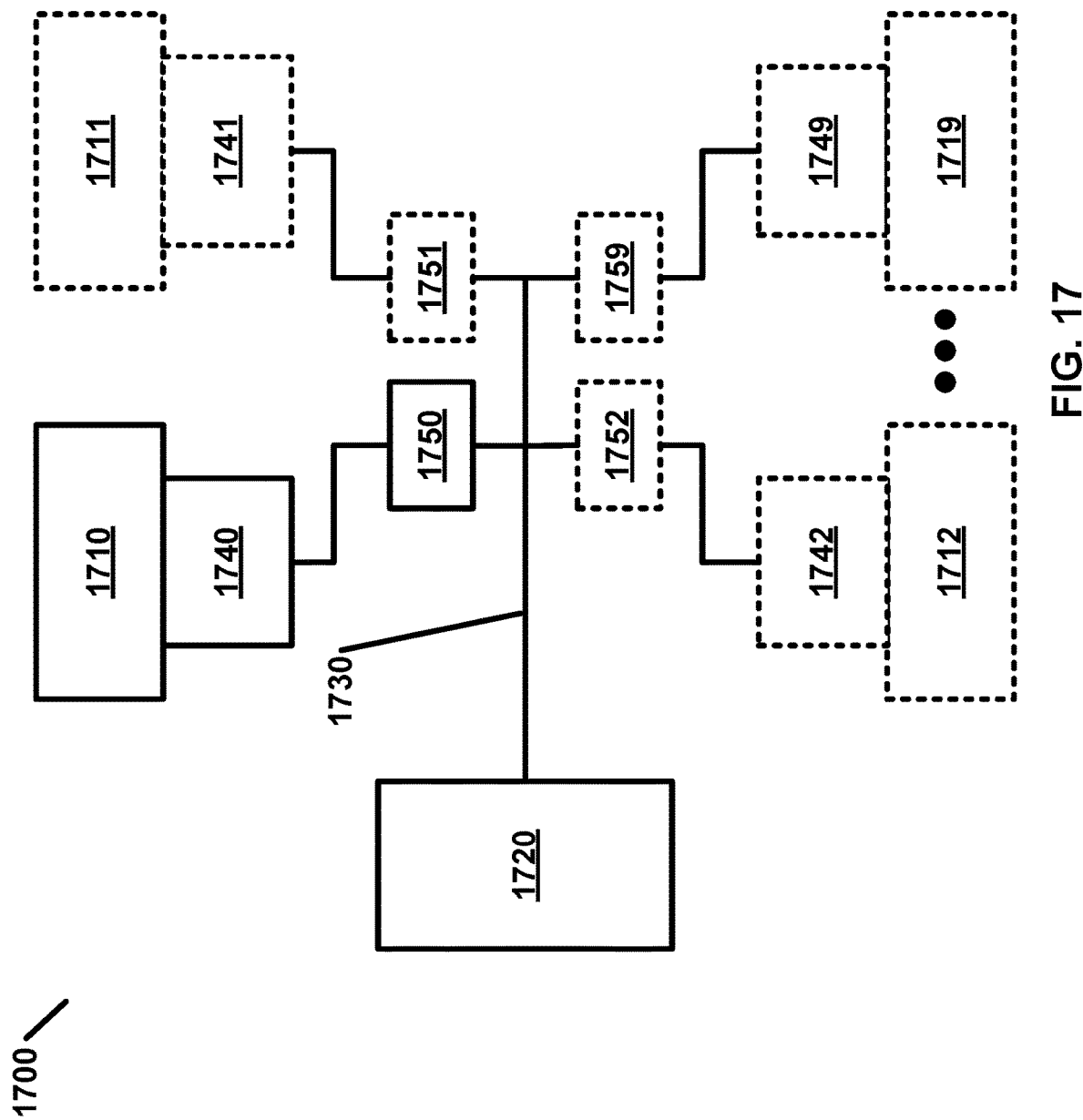
FIG. 17 is a block diagram showing a wearable emergency hemorrhage cessation system as per an aspect of various embodiments.

FIG. 17 is a block diagram showing a wearable emergency hemorrhage cessation system as per an aspect of various embodiments. The wearable emergency hemorrhage cessation system 1700 may comprise at least one tourniquet (e.g. 1710, 1711, 1712 . . . 1719). Each of the at least one tourniquet (e.g. 1710, 1711, 1712 . . . 1719) may comprise an actuator (e.g. 1740, 1741, 1742 . . . 1749). The wearable emergency hemorrhage cessation system 1700 may comprise at least one power source 1720 and at least one switch (e.g. 1750, 1751, 1752 . . . 1759). The at least one power source 1720 may be wearable. The at least one power source 1720 may be electrically connected to the at least one switch (e.g. 1750, 1751, 1752 . . . 1759) through employment of power leads 1730. Each of the at least one switch (e.g. 1750, 1751, 1752 . . . 1759) may be configured to cause a power transfer from the at least one power source 1720 to one of at least one actuator (e.g. 1740, 1741, 1742 . . . 1749).

Figure 18:
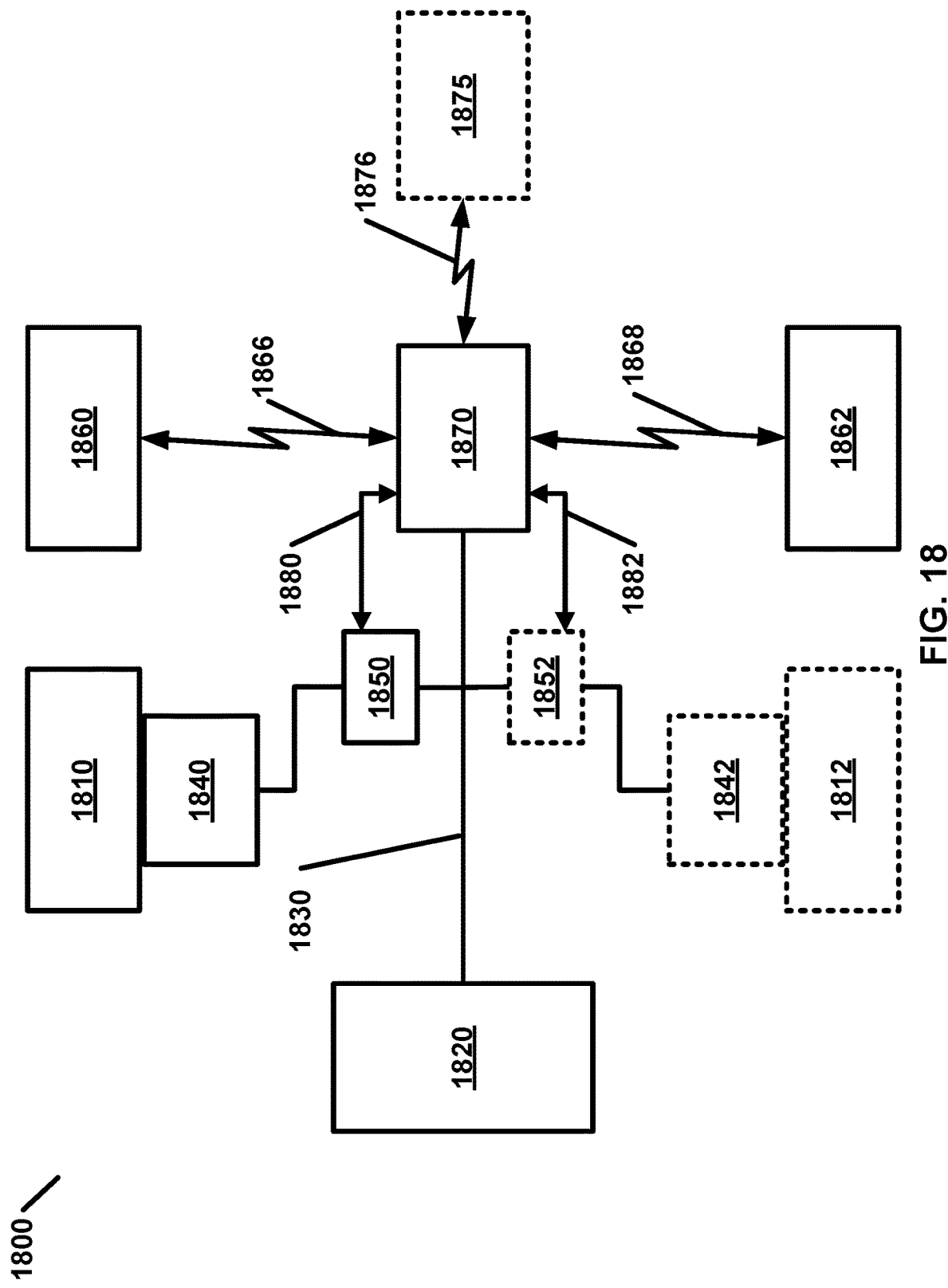
FIG. 18 is a block diagram showing a wearable emergency hemorrhage cessation system as per an aspect of various embodiments.

FIG. 18 is a block diagram showing a wearable emergency hemorrhage cessation system as per an aspect of various embodiments. The wearable emergency hemorrhage cessation system 1800 may comprise at least one tourniquet (e.g. 1810 and 1812). Each of the at least one tourniquet (e.g. 1810 and 1812) may comprise an actuator (e.g. 1840 and 1842). The wearable emergency hemorrhage cessation system 1800 may comprise at least one power source 1820 and at least one switch (e.g. 1850 and 1852). The at least one power source 1820 may be wearable. The at least one power source 1820 may be electrically connected to the at least one switch (e.g. 1850 and 1852) through employment of power leads 1830. Each of the at least one switch (e.g. 1850 and 1852) may be configured to cause a power transfer from the at least one power source 1820 to one of at least one actuator (e.g. 1840 and 1842). At least one of the at least one switch may be configured to cause a power transfer to one of the at least one actuator after at least one of the at least one tourniquet is fitted to the wearer. The wearable emergency hemorrhage cessation system 1800 may comprise at least one physiological sensor (e.g. 1860 and 1862) and a processing unit 1870. The processing unit 1870 may be configured to communicate with the at least one physiological sensor (e.g. 1860 and 1862). At least one communication channel (e.g. 1866 and 1868) may be employed for communication between the processing unit 1870 and the at least one physiological sensor (e.g. 1860 and 1862). The processing unit 1870 may be configured to communicate with the at least one switch (e.g. 1850 and 1852). At least one electrical signal (e.g. 1880 and 1882) may be employed for communication between the processing unit 1870 and the at least one switch (e.g. 1850 and 1852). The processing unit may be configured to communicate with a remote device 1875. At least one communication channel 1876 may be employed for communication between the processing unit 1870 and the remote device 1875.

Figure 19B:
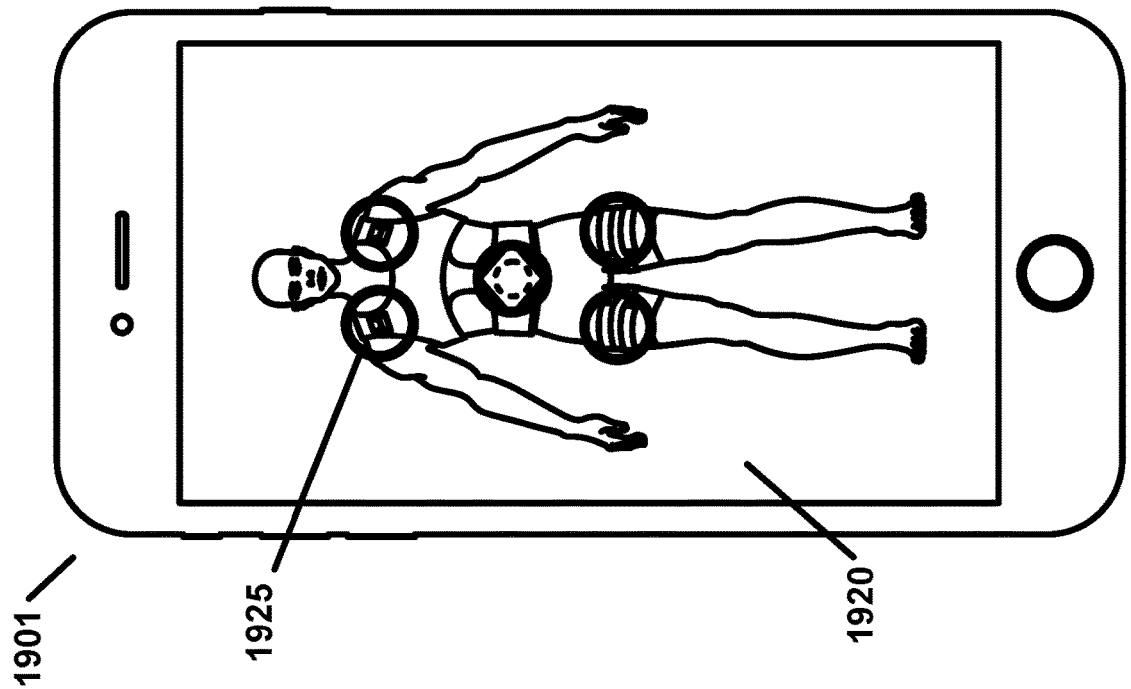
FIGS. 19A and 19B illustrate remote devices in communication with a wearable emergency hemorrhage cessation system as per aspects of various embodiments.
Figure 19A:
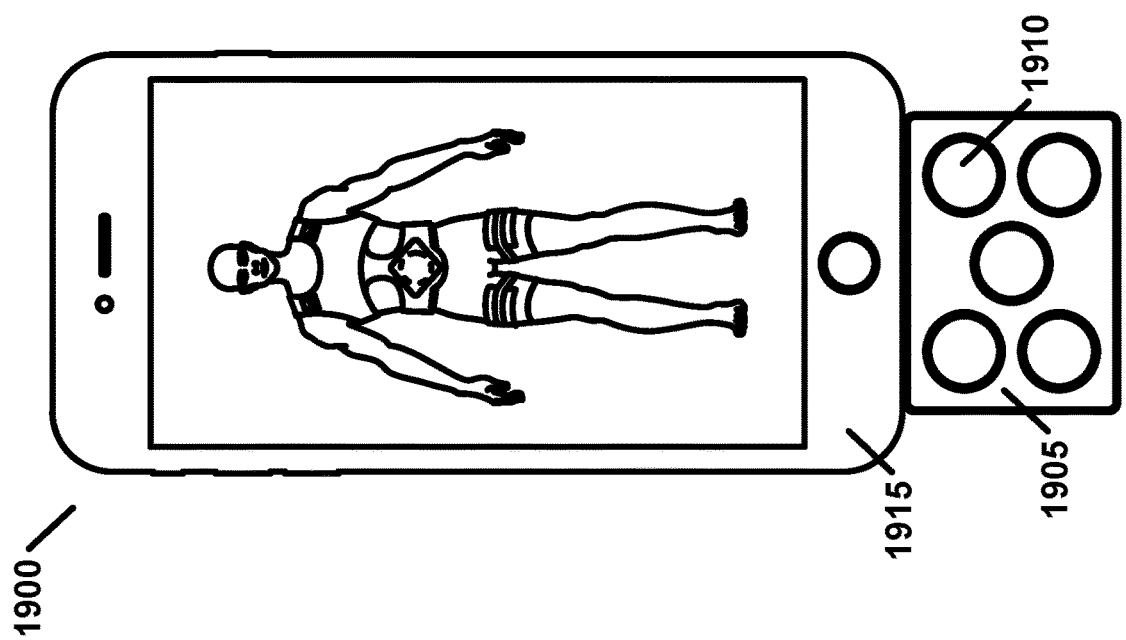

FIG. 19A illustrates a remote device in communication with a wearable emergency hemorrhage cessation system as per an aspect of various embodiments. The remote device 1900 may comprise at least one user interface. One of the at least one user interface may be configured as a button interface 1905. The button interface 1905 may be configured as an accessory to a computing device 1915. The button interface 1905 may be configured to communicate with the computing device 1915 through employment of a communications port on the computing device 1915. The communications port may, for example, comprise a headset port, a power port, a USB port, combinations thereof, and/or the like. The button interface 1905 may be configured with a plurality of buttons (e.g. 1910). Each of the plurality of buttons (e.g. 1910) may correspond to a switch in the wearable hemorrhage cessation system. Upon activation of one of the plurality of buttons (e.g. 1910), the remote device 1900 may be configured to communicate a command to the wearable emergency hemorrhage cessation system. The command may be configured to cause activation of a tourniquet associated with the switch.

FIG. 19B illustrates a remote device in communication with a wearable emergency hemorrhage cessation system as per an aspect of various embodiments. The remote device 1901 may comprise at least one user interface. One of the at least one user interface may be configured as a touch input display 1920. The remote device 1901 may be programmed to display an interactive emergency hemorrhage cessation system comprising a plurality of soft buttons (e.g. 1925). Each of the plurality of soft buttons (e.g. 1925) may correspond to a switch in the wearable hemorrhage cessation system. Upon activation of one of the plurality of soft buttons (e.g. 1925), the remote device 1901 may be configured to communicate a command to the wearable emergency hemorrhage cessation system. A soft button may be implemented with a combination of hardware and programmable instructions. The hardware may comprise a touch screen. The programmable instructions may implement an action (e.g. send a command) when a portion of the touch screen is contacted. The portion of the screen may be aligned with an image (e.g. as illustrated by example element 1925 in FIG. 19B). The command may be configured to cause activation of a tourniquet associated with the switch.

Some of the various embodiments may comprise a method of employing a wearable system. The method may comprise donning the wearable system. The wearable system may comprise at least one tourniquet. Each of the at least one tourniquet may comprise an actuator. Each of the at least one tourniquet may be configured to occlude blood flow in at least one artery of a wearer of the wearable system. The wearable system may comprise a wearable power source. The method may comprise activating a switch. The switch may be configured to cause a power transfer from the at least one power source to the actuator.

According to some of the various embodiments, a method of employing a wearable system may comprise adjusting at least one adjustable component. Each of the at least one adjustable component may be associated with one of at least one tourniquet. Each of the at least one adjustable component may be distinct from an actuator. Each of the at least one adjustable component may comprise a strap, a cable, a cord, a buckle, a clamp, a ring, combinations thereof, and/or the like. The method of employing a wearable system may comprise attaching the actuator to the wearable system. The method of employing a wearable system may comprise receiving, at a processing unit, at least one physiological signal from at least one physiological sensor. The method of employing a wearable system may comprise communicating at least one command from the processing unit to a switch. The at least one command may be based, at least in part, on at least one of the at least one physiological signal. The method of employing a wearable system may comprise activating the switch based, at least in part, on the at least one command.

Figure 20:
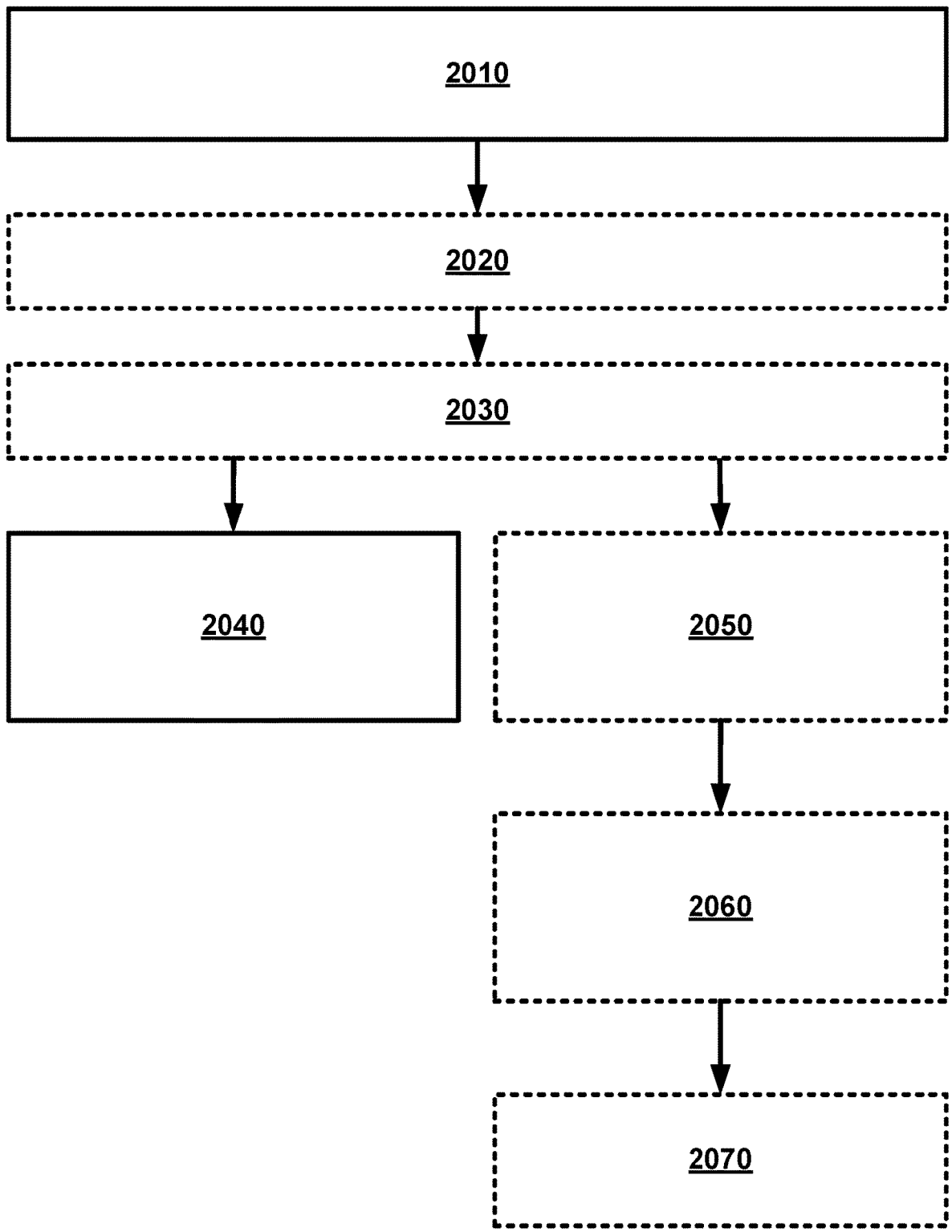
FIG. 20 is an example flow diagram of employing a wearable emergency hemorrhage cessation system as per an aspect of various embodiments.

FIG. 20 is an example flow diagram of employing a wearable emergency hemorrhage cessation system as per an aspect of various embodiments. A wearable system may be donned at 2010. The wearable system may comprise a tourniquet(s) and a power source(s). The tourniquet(s) may comprise an actuator(s). An adjustable component(s) associated with at least one of the tourniquet(s) may be adjusted at 2020. The actuator(s) may be attached to the wearable system at 2030. A switch(es) configured to cause a power transfer from a power source(s) to an actuator(s) may be activated at 2040. A physiological signal(s) may be received from a physiological sensor(s) at 2050. The physiological signal(s) may be received at a processing unit. A command(s) may be communicated from the processing unit to the switch at 2060. The command(s) may be based, at least in part, on the physiological signal(s). The switch(es) may be activated at 2070 based, at least in part, on the command(s).

According to some of the various embodiments, a wearable system may comprise at least one tourniquet. Each of at least one tourniquet may comprise an activator. Each of the at least one activator may be configured to activate one of the at least one tourniquet. The wearable system may comprise a processing unit. The processing unit may be configured to communicate with the at least one activator. The wearable system may comprise a receiving unit. The receiving unit may be configured to communicate with at least one remote device. The receiving unit may be configured to communicate with the processing unit. The wearable system may comprise a tangible non-transitory computer readable medium. The computer readable medium may comprise instructions configured to cause the processing unit to receive at least one assessment command from the receiving unit. The at least one assessment command may be communicated from the at least one remote device. The computer readable medium may comprise instructions configured to cause the processing unit to create at least one activator signal. The at least one activator signal may be based, at least in part, on the at least one assessment command. The computer readable medium may comprise instructions configured to cause the processing unit to communicate each of the at least one activator signal to one of the at least one activator.

According to some of the various embodiments, each of at least one tourniquet may comprise at least one adjustable component distinct from an activator. The at least one adjustable component may comprise a strap, a cable, a cord, a buckle, a clamp, a ring, combinations thereof, and/or the like. A strap, cable, cord, combinations thereof, and/or the like may be coupled to the activator.

According to some of the various embodiments, each of at least one activator may comprise a valve. Each of at least one tourniquet may comprise an inflatable chamber. A wearable system may comprise at least one compressed gas source in fluid communication with the valve and the inflatable chamber.

According to some of the various embodiments, each of at least one activator may comprise an actuator. Each of at least one tourniquet may comprise a strap, a cable, a cord, combinations thereof, and/or the like coupled to the actuator. A wearable system may comprise at least one wearable power source. The at least one wearable power source may be configured to supply power to at least one of the at least one activator, a processing unit, and/or a receiving unit.

According to some of the various embodiments, a wearable system may comprise at least one switch. At least one of the at least one switch may be configured for mechanical operation. At least one of the at least one switch may be configured to communicate a mechanical signal to one of at least one activator.

Figure 21:
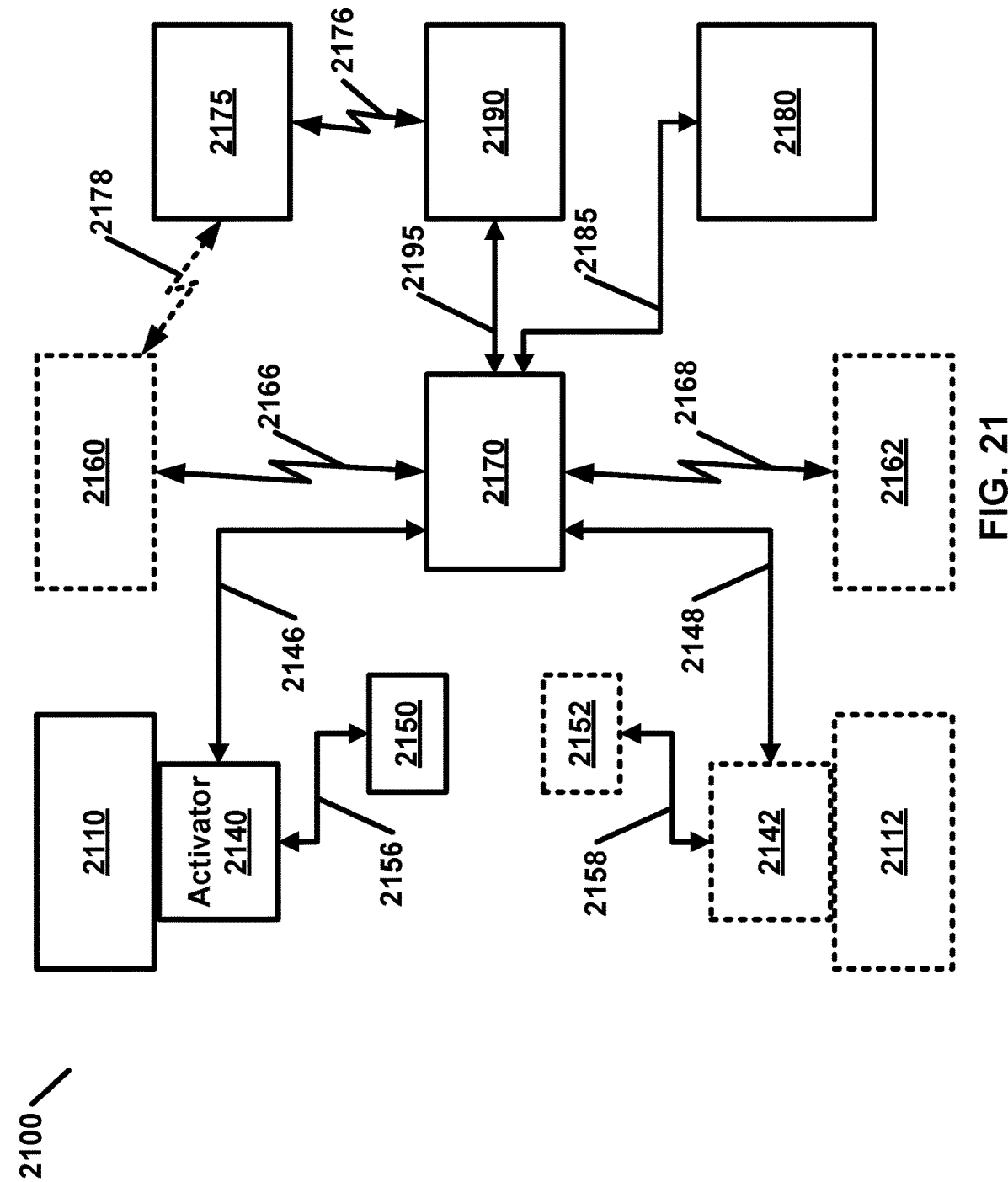
FIG. 21 is a block diagram showing a wearable emergency hemorrhage cessation system as per an aspect of various embodiments.

FIG. 21 is a block diagram showing a wearable emergency hemorrhage cessation system as per an aspect of various embodiments. The wearable emergency hemorrhage cessation system 2100 may comprise at least one tourniquet (e.g. 2110 and 2112). Each of the at least one tourniquet (e.g. 2110 and 2112) may comprise an activator (e.g. 2140 and 2142). The wearable emergency hemorrhage cessation system 2100 may comprise at least one switch (e.g. 2150 and 2152). Each of the at least one switch (e.g. 2150 and 2152) may be configured to communicate with an activator (e.g. 2140 and 2142). At least one electrical signal (e.g. 2156 and 2158) may be employed for communication between one of the at least one switch (e.g. 2150 and 2152) and one of the at least one activator (e.g. 2140 and 2142). The wearable emergency hemorrhage cessation system 2100 may comprise at least one physiological sensor (e.g. 2160 and 2162) and a processing unit 2170. The processing unit 2170 may be configured to communicate with the at least one physiological sensor (e.g. 2160 and 2162). At least one communication channel (e.g. 2166 and 2168) may be employed for communication between the processing unit 2170 and the at least one physiological sensor (e.g. 2160 and 2162). The processing unit 2170 may be configured to communicate with the at least one activator (e.g. 2140 and 2142). At least one electrical signal (e.g. 2146 and 2148) may be employed for communication between the processing unit 2170 and the at least one activator (e.g. 2140 and 2142). The wearable emergency hemorrhage cessation system 2100 may comprise a computer readable medium 2180 and a receiving unit 2190. At least one electrical signal 2185 may be employed for communication between the computer readable medium 2180 and the processing unit 2170. At least one electrical signal 2195 may be employed for communication between the receiving unit 2190 and the processing unit 2170. The receiving unit 2190 may be configured to communicate with at least one remote device (e.g. 2175). At least one communication channel (e.g. 2176) may be employed for communication between the receiving unit 2190 and the at least one remote device (e.g. 2175). At least one communication channel (e.g. 2178) may be employed for communication between the at least one remote device (e.g. 2175) and at least one of the at least one physiological sensor (e.g. 2160).

Figure 22:
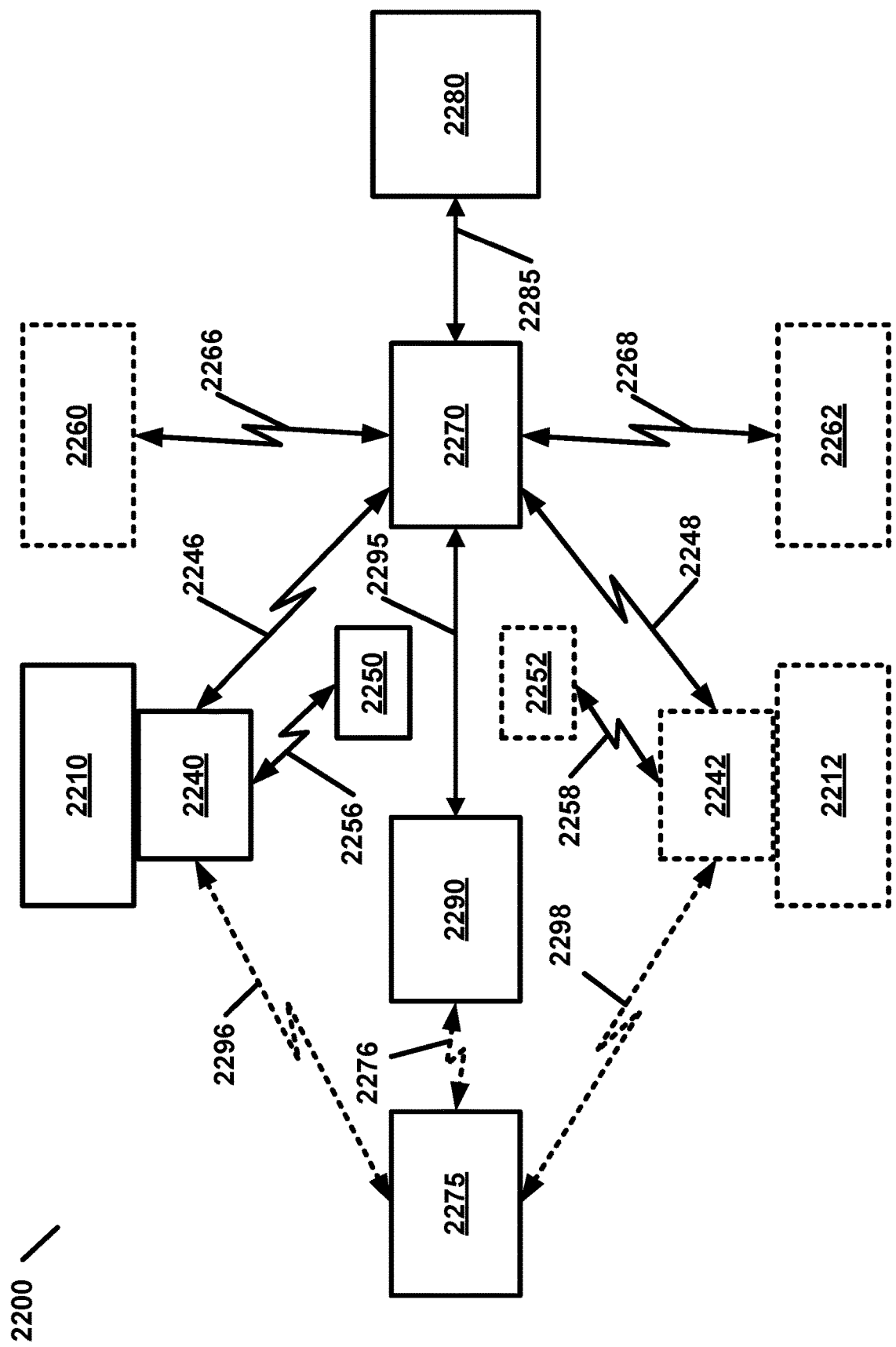
FIG. 22 is a block diagram showing a wearable emergency hemorrhage cessation system as per an aspect of various embodiments.

FIG. 22 is a block diagram showing a wearable emergency hemorrhage cessation system as per an aspect of various embodiments. The wearable emergency hemorrhage cessation system 2200 may comprise at least one tourniquet (e.g. 2210 and 2212). Each of the at least one tourniquet (e.g. 2210 and 2212) may comprise an activator (e.g. 2240 and 2242). The wearable emergency hemorrhage cessation system 2200 may comprise at least one switch (e.g. 2250 and 2252). Each of the at least one switch (e.g. 2250 and 2252) may be configured to communicate with an activator (e.g. 2240 and 2242). At least one communication channel (e.g. 2256 and 2258) may be employed for communication between at least one of the at least one switch (e.g. 2250 and 2252) and at least one of the at least one activator (e.g. 2240 and 2242). The wearable emergency hemorrhage cessation system 2200 may comprise at least one physiological sensor (e.g. 2260 and 2262) and a processing unit 2270. The processing unit 2270 may be configured to communicate with the at least one physiological sensor (e.g. 2260 and 2262). At least one communication channel (e.g. 2266 and 2268) may be employed for communication between the processing unit 2270 and the at least one physiological sensor (e.g. 2260 and 2262). The processing unit 2270 may be configured to communicate with the at least one activator (e.g. 2240 and 2242). At least one communication channel (e.g. 2246 and 2248) may be employed for communication between the processing unit 2270 and the at least one activator (e.g. 2240 and 2242). The wearable emergency hemorrhage cessation system 2200 may comprise a computer readable medium 2280 and a receiving unit 2290. At least one electrical signal 2285 may be employed for communication between the computer readable medium 2280 and the processing unit 2270. At least one electrical signal 2295 may be employed for communication between the receiving unit 2290 and the processing unit 2270. The receiving unit 2290 may be configured to communicate with at least one remote device (e.g. 2275). At least one communication channel (e.g. 2276) may be employed for communication between the receiving unit 2290 and the at least one remote device (e.g. 2275). Each of the at least one activator (e.g. 2240 and 2242) may be configured to receive commands directly from at least one of the at least one remote device (e.g. 2275). At least one communication channel (e.g. 2296 and 2298) may be employed for communication between the at least one activator (e.g. 2240 and 2242) and at least one of the at least one remote device (e.g. 2275).

Some of the various embodiments may comprise a method of communication between a remote device and a wearable emergency hemorrhage cessation system. The method may comprise detecting at least one hemorrhage in a wearer of the emergency hemorrhage cessation system. The emergency hemorrhage cessation system may comprise at least one tourniquet. The method may comprise identifying a location on the body of the wearer associated with each of the at least one hemorrhage. The method may comprise creating at least one assessment command Each of the at least one assessment command may be based, at least in part, on the location on the body associated with the one of the at least one hemorrhage. The method may comprise communicating the at least one assessment command to the emergency hemorrhage cessation system. The method may comprise causing activation of at least one of the at least one tourniquet. Activation of the at least one of the at least one tourniquet may be based, at least in part, on the at least one assessment command. For example, a remote device may detect a hemorrhage in the right arm of the wearer. The remote device may create and communicate an assessment command to the emergency hemorrhage cessation system. The emergency hemorrhage cessation system may receive the assessment command and activate the tourniquet proximal to the right arm of the wearer. In another example, a second party may detect a hemorrhage in the left shoulder of the wearer. The second party may employ a remote device to create and communicate an assessment command to the emergency hemorrhage cessation system. The emergency hemorrhage cessation system may receive the assessment command and activate the junctional tourniquet at the left shoulder of the wearer.

According to some of the various embodiments, a method may comprise employing at least one imaging device to detect at least one hemorrhage. The at least one imaging device may be configured to detect a wound, injury, missing appendage, blood, combinations thereof, and/or the like. The method may comprise analyzing at least one image to detect a wound, injury, missing appendage, blood, combinations thereof, and/or the like. The method may comprise employing at least one imaging device to identify a location on the body. The method may comprise analyzing at least one image to identify a location on the body. The method may comprise employing at least one blood detection sensor to detect the at least one hemorrhage. The blood detection sensor may, for example, comprise an infrared scanner, an infrared camera, a thermal scanner, a thermal camera, combinations thereof, and/or the like. The method may comprise analyzing data from the camera and/or scanner to detect the at least one hemorrhage. The method may comprise employing at least one blood detection sensor to identify a location on the body. The method may comprise analyzing data from the camera and/or scanner to identify a location on the body.

Some of the various embodiments may comprise a method of communication between a remote device and a wearable emergency hemorrhage cessation system. The method may comprise receiving at least one physiological signal from the wearable emergency hemorrhage cessation system. The method may comprise creating at least one remote command. Each of the at least one remote command may be based, at least in part, on at least one of the at least one physiological signal. The method may comprise communicating the at least one remote command to the wearable emergency hemorrhage cessation system. The method may comprise causing activation of at least one of at least one tourniquet. Activation of at least one of the at least one tourniquet may be based, at least in part, on the at least one remote command. The method may comprise receiving location information from the wearable emergency hemorrhage cessation system. The method may comprise communicating the location information to at least one remote device. For example, a first remote device may comprise a smartphone. The first remote device may be configured to receive location information from the wearable emergency hemorrhage cessation system. In the case that no location information is received from the wearable emergency hemorrhage cessation system, the first remote device may be configured to create location information based on a location of the first remote device. In this example, the first remote device may be configured to communicate the location information to a second remote device such as, for example, a network server configured to receive distress signals. In another example, a first remote device may comprise an unmanned vehicle. The first remote device may be configured to receive location information from the wearable emergency hemorrhage cessation system. In this example, the first remote device may be configured to communicate the location information to a second remote device such as, for example, a mobile device configured to communicate with a communication system (e.g. Nett Warrior or Blue Force Tracking). By way of example and not limitation, the unmanned vehicle may comprise an unmanned aerial vehicle (e.g. a drone), or a robot (e.g. a rover).

According to some of the various embodiments, a wearable emergency hemorrhage cessation system may be configured to communicate at least one alert to a remote device. The at least one alert may comprise data associated with information transmitted from at least one physiological sensor, a system fault, loss of communication with at least one system component, acknowledgement of at least one remote command, combinations thereof, and/or the like.

Figure 23:
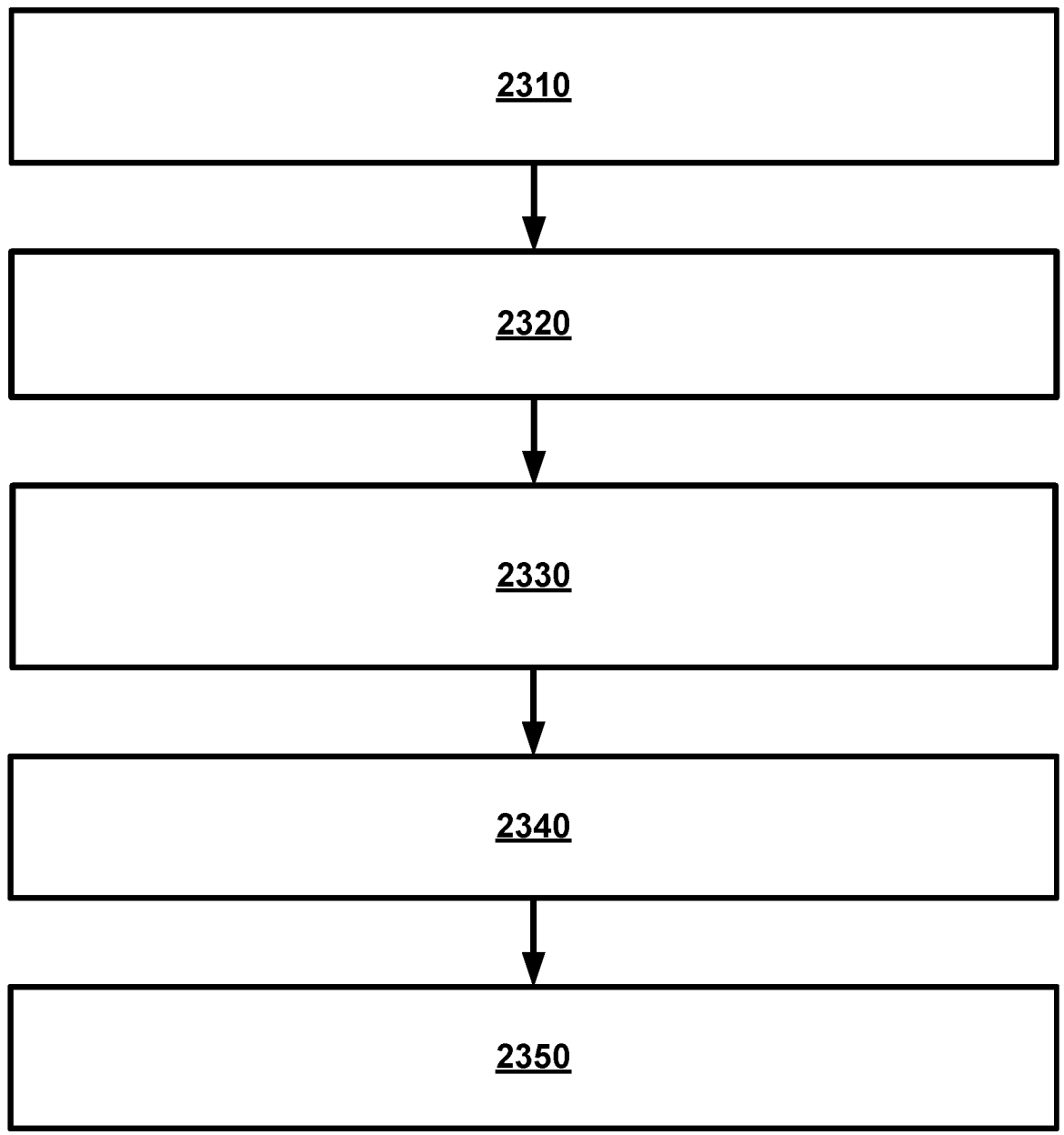
FIG. 23 is an example flow diagram of communication with a wearable emergency hemorrhage cessation system as per an aspect of an embodiment.

FIG. 23 is an example flow diagram of communication with a wearable emergency hemorrhage cessation system as per an aspect of an embodiment. At least one hemorrhage may be detected in a wearer of an emergency hemorrhage cessation system at 2310. The emergency hemorrhage cessation system may comprise at least one tourniquet. A location on the body of the wearer may be identified at 2320. The location may be associated with each of the at least one hemorrhage. At least one assessment command may be created at 2330. Each of the at least one assessment command may be based, at least in part, on the location on the body of the wearer. The at least one assessment command may be communicated to the emergency hemorrhage cessation system at 2340. Activation of at least one of the at least one tourniquet may be caused at 2350. The activation may be based, at least in part, on the at least one assessment command.

Figure 24:
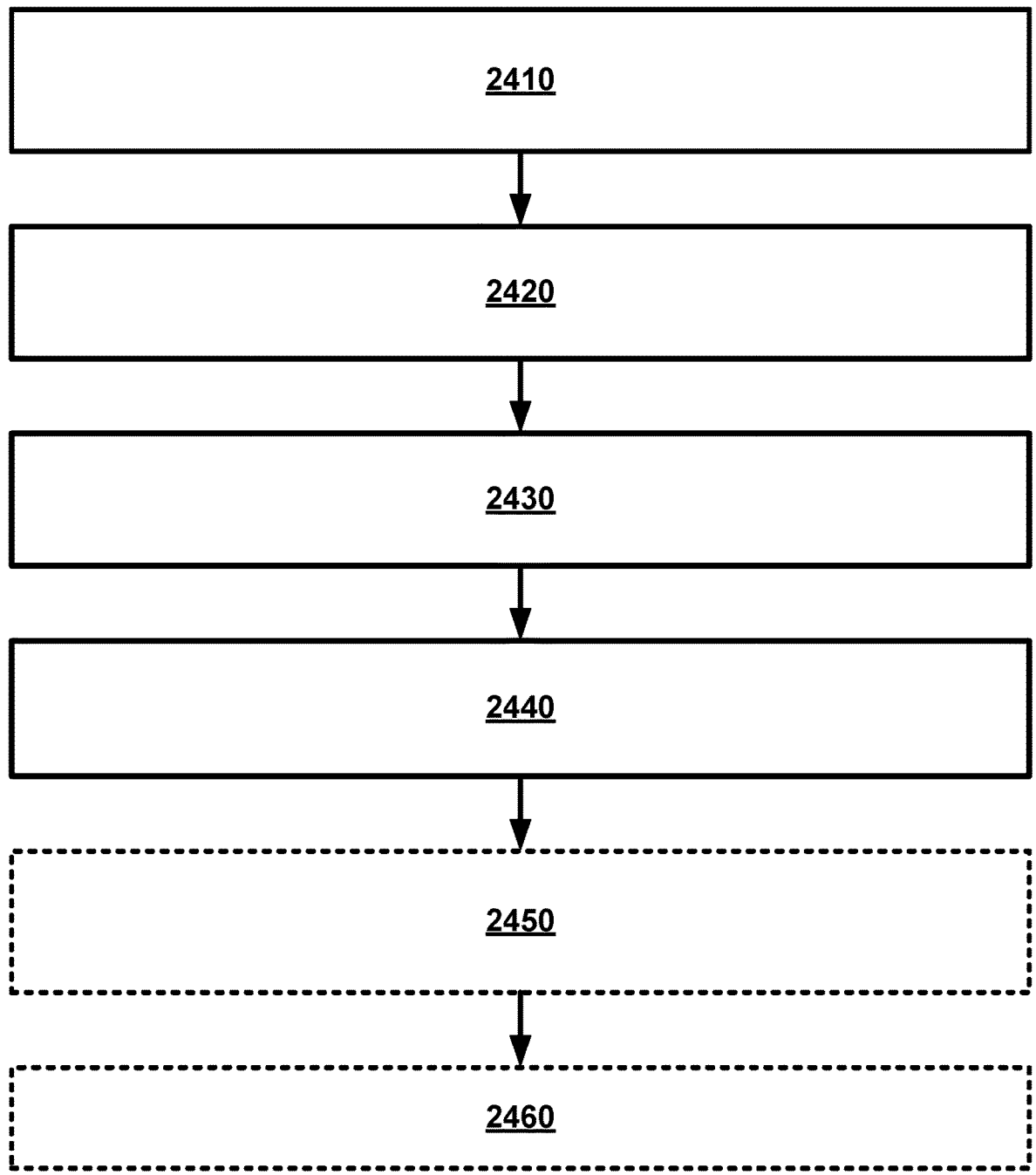
FIG. 24 is an example flow diagram of communication with a wearable emergency hemorrhage cessation system as per an aspect of various embodiments.

FIG. 24 is an example flow diagram of communication with a wearable emergency hemorrhage cessation system as per an aspect of various embodiments. At least one physiological signal may be received from a wearable emergency hemorrhage cessation system at 2410. The wearable emergency hemorrhage cessation system may comprise at least one tourniquet. At least one remote command may be crated at 2420. Each of the at least one remote command may be based, at least in part, on at least one of the at least one physiological signal. The at least one remote command may be communicated to the wearable emergency hemorrhage cessation system at 2430. Activation of at least one of the at least one tourniquet may be caused at 2440. The activation may be based, at least in part, on the at least one remote command Location information may be received from the wearable emergency hemorrhage cessation system at 2450. The location information may be communicated to at least one remote device at 2460.

According to some of the various embodiments, a method of communication between a remote device and a wearable emergency hemorrhage cessation system may comprise receiving location information of a first location. The information of a first location may be communicated from a device in communication with the wearable emergency hemorrhage cessation system. The device may employ a first wireless channel for communication with the wearable emergency hemorrhage cessation system. The method may comprise guiding an unmanned vehicle to a second location within a communication range of the first location. The communication range may be based on a second wireless channel. The method may comprise receiving at least one physiological signal at a receiving unit associated with the unmanned vehicle. The at least one physiological signal may be received through employment of the second wireless channel. The method may comprise creating at least one remote command employing a processing unit located with the unmanned vehicle. The method may comprise communicating the at least one remote command employing a transmitting unit located with the unmanned vehicle. The first wireless channel and/or the second wireless channel may be configured for encrypted communication. For example, a first remote device may comprise a network device associated with a communication system. The first remote device may be configured to receive location information from the wearable emergency hemorrhage cessation system. In this example, the first remote device may employ a first wireless channel to communicate with the communication system. By way of example and not limitation, the first wireless channel may be configured for an effective communication range that is greater than the second wireless channel.

Figure 25:
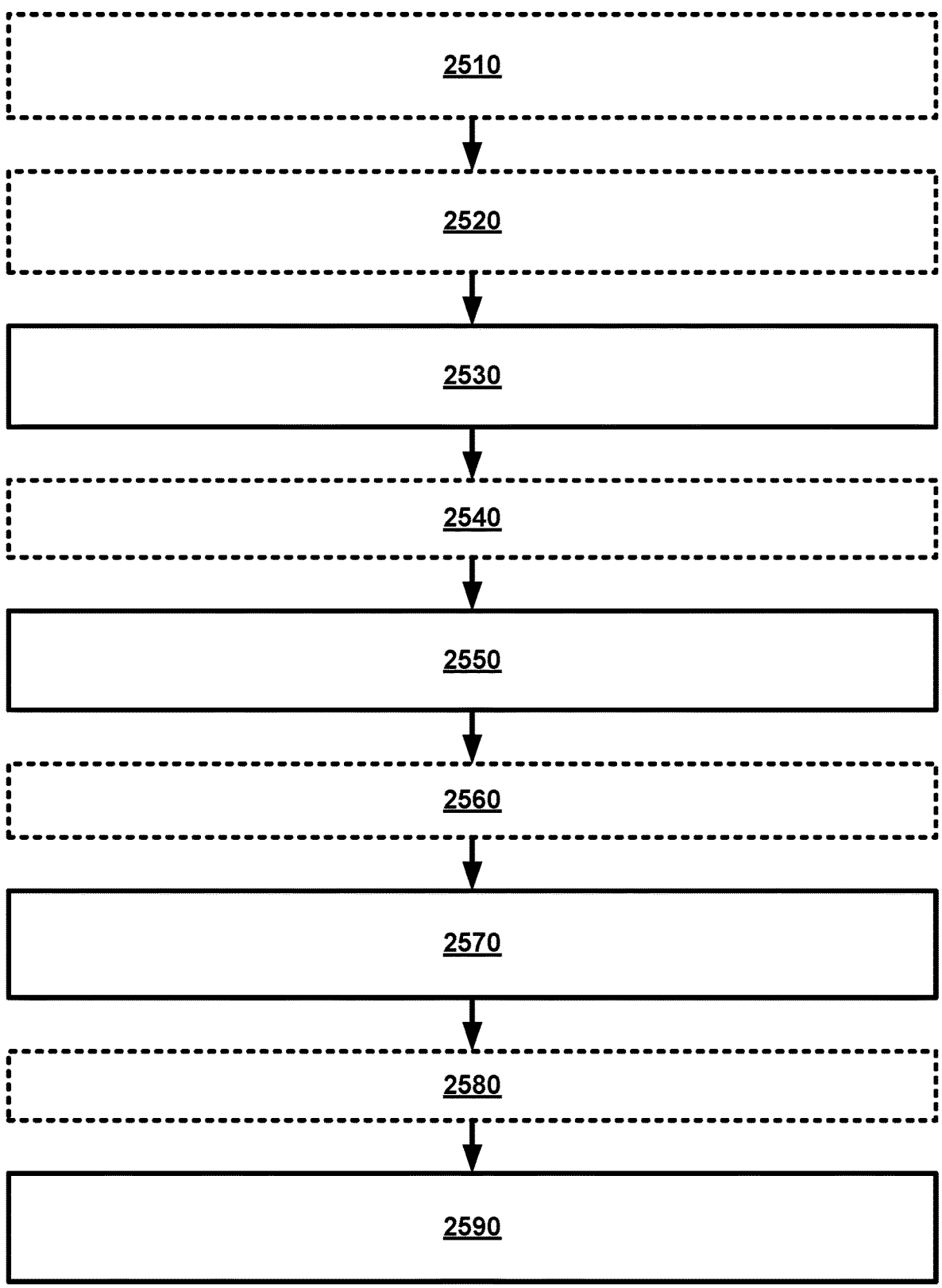
FIG. 25 is an example flow diagram of communication with a wearable emergency hemorrhage cessation system as per an aspect of various embodiments.

FIG. 25 is an example flow diagram of communication with a wearable emergency hemorrhage cessation system as per an aspect of various embodiments. Location information of a first location may be received at 2510. The location information may be communicated from a device in communication with a wearable emergency hemorrhage cessation system. An unmanned vehicle may be guided to a second location at 2520. The second location may be located within a communication range of the first location. At least one physiological signal may be received from a wearable emergency hemorrhage cessation system at 2530. The wearable emergency hemorrhage cessation system may comprise at least one tourniquet. The at least one physiological signal may be received at a receiving unit at 2540. At least one remote command may be created at 2550. Each of the at least one remote command may be based, at least in part, on at least one of the at least one physiological signal. The at least one remote command may be created employing a processing unit at 2560. The at least one remote command may be communicated to the wearable emergency hemorrhage cessation system at 2570. The at least one remote command may be communicated employing a transmitting unit at 2580. Activation of at least one of the at least one tourniquet may be caused at 2590. The activation may be based, at least in part, on the at least one remote command.

Figure 26:
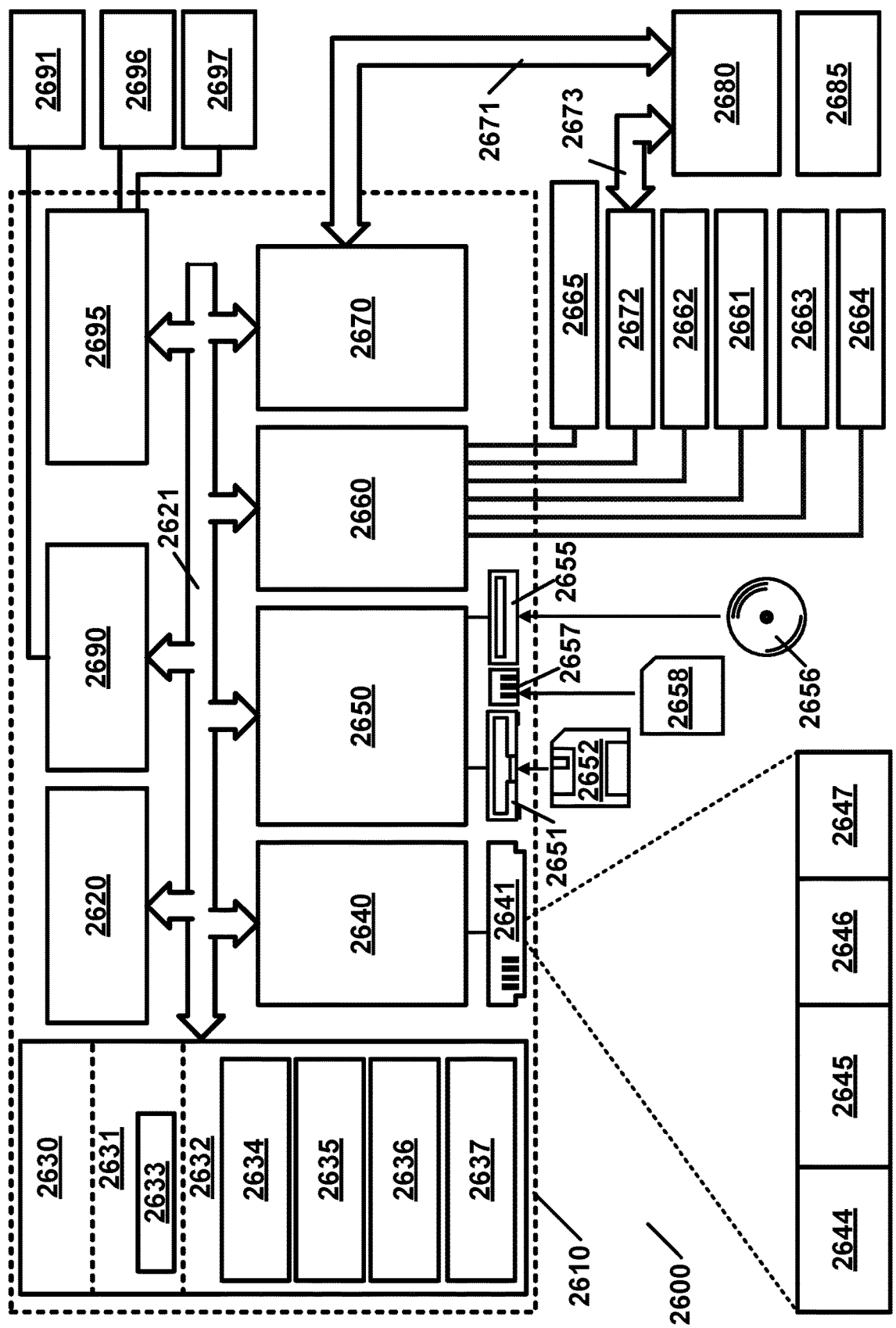
FIG. 26 is a block diagram of a computing environment in which aspects of embodiments of the present invention may be practiced.

FIG. 26 illustrates an example system for implementing at least some embodiments and comprises a general-purpose computing device in the form of a computing device 2610. Components of computing device 2610 may include, but are not limited to, a processing unit 2620, a system memory 2630, and a system bus 2621 that couples various system components including the system memory 2630 to the processing unit 2620.

Computing device 2610 may comprise a variety of computer readable media. Computer readable media may be available media accessible by computing device 2610 and may include both volatile and nonvolatile media, removable and non-removable media. By way of example, and not limitation, computer readable media may comprise computer storage media and communication media. Computer storage media may comprise both volatile and nonvolatile, removable and non-removable media implemented in a method or technology for storage of information such as computer readable instructions, data structures, program modules, other data, combinations thereof, and/or the like. Computer storage media may comprise, but is not limited to, random access memory (RAM), read-only memory (ROM), electrically erasable programmable read-only memory (EEPROM), flash memory or other memory technology, compact disc read-only memory (CD-ROM), digital versatile disks (DVD) or other optical disk storage, magnetic cassettes, magnetic tape, magnetic disk storage or other magnetic storage devices, and/or any other medium which may be employed to store information and which may be accessed by computer 2610. Communication media may comprise computer readable instructions, data structures, program modules and/or other data in a modulated data signal such as a carrier wave and/or other transport mechanism and may comprise information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above may also be included within the scope of computer readable media.

The system memory 2630 may comprise computer storage media in the form of volatile and/or nonvolatile memory such as ROM 2631 and RAM 2632. A basic input/output system 2633 (BIOS), containing the basic routines that help to transfer information between elements within computer 2610, such as during start-up, may be stored in ROM 2631. RAM 2632 may comprise data and/or program modules that may be accessible to and/or presently being operated on by processing unit 2620. By way of example, and not limitation, FIG. 26 illustrates operating system 2634, application programs 2635, other program modules 2636, and program data 2637.

The computing device 2610 may also comprise other removable/non-removable volatile/nonvolatile computer storage media. By way of example only, FIG. 26 illustrates a hard disk drive 2641 that may read from or write to non-removable, nonvolatile magnetic media, a magnetic disk drive 2651 that may read from or write to a removable, nonvolatile magnetic disk 2652, a flash drive reader 2657 that may read flash drive 2658, and an optical disk drive 2655 that may read from or write to a removable, nonvolatile optical disk 2656 such as a CD ROM or other optical media.

Other removable/non-removable, volatile/nonvolatile computer storage media that may be used in the operating environment include, but are not limited to, magnetic tape cassettes, flash memory cards, digital versatile disks, digital video tape, solid state RAM, solid state ROM, and the like. The hard disk drive 2641 may be connected to the system bus 2621 through a non-removable memory interface such as interface 2640, and magnetic disk drive 2651 and optical disk drive 2655 may be connected to the system bus 2621 by a removable memory interface, such as interface 2650.

The drives and their associated computer storage media discussed above and illustrated in FIG. 26 provide storage of computer readable instructions, data structures, program modules and other data for the computer 2610. In FIG. 26, for example, hard disk drive 2641 is illustrated as storing operating system 2644, application programs 2645, program data 2647, and other program modules 2646. Additionally, for example, non-volatile memory may include instructions for presenting images on a display 2691 of computing device 2600 and/or the like. Similarly, non-volatile memory may comprise instructions for causing the presentation of images on the display of a remote computing device 2680 and/or the like. Display 2691 and touch input 2665 may be integrated into the same device.

A user may enter commands and information into computing device 2610 through input devices such as a touch input device 2665, a keyboard 2662, a microphone 2663, a camera 2664, and a pointing device 2661, such as a mouse, trackball or touch pad. These and other input devices may be connected to the processing unit 2620 through a input interface 2660 coupled to system bus 2621, but may be connected by other interface and bus structures, such as a parallel port, game port or a universal serial bus (USB). A display 2691 or other type of display device may be connected to the system bus 2621 via an interface, such as a video interface 2690. Other devices, such as, for example, speakers 2697 and printer 2696 may be connected to the system via output interface 2695.

The computing device 2610 may be operated in a networked environment using logical connections to one or more remote computers, such as a remote computer 2680. Remote computer 2680 may be a personal computer, a hand-held device, a server, a router, a network PC, a peer device or other common network node, and typically includes many or all of the elements described above relative to the computing device 2610. The logical connections depicted in FIG. 26 include a local area network (LAN) 2671 and a wide area network (WAN) 2673, but may also include other networks. Such networking environments are commonplace in offices, enterprise-wide computer networks, intranets and the Internet.

When used in a LAN networking environment, the computing device 2610 is connected to the LAN 2671 through a network interface or adapter 2670. When used in a WAN networking environment, the computing device 2610 may comprise a modem 2672 or other means for establishing communications over the WAN 2673, such as the Internet. The modem 2672, which may be internal or external, may be connected to the system bus 2681 via interface 2660, or other appropriate mechanism. The modem 2672 may be wired or wireless. Examples of wireless devices may comprise, but are not limited to: Wi-Fi and Bluetooth. In a networked environment, program modules depicted relative to the computing device 2610, or portions thereof, may be stored in the remote memory storage device. By way of example, and not limitation, FIG. 26 illustrates remote application programs 2685 as residing on remote computer 2680. It will be appreciated that the network connections shown are presented as examples only and other means of establishing a communications link between the computers may be used.

Although the subject matter has been described in language specific to system features and/or instructions, it is to be understood that the subject matter defined in the appended claims is not necessarily limited to the specific features or instructions described above. Rather, the specific features and instructions described above are disclosed as example forms of implementing the claims.

In this specification, "a" and "an" and similar phrases are to be interpreted as "at least one" and "one or more." References to "an" embodiment in this disclosure are not necessarily to the same embodiment.

Many of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, wetware (i.e. hardware with a biological element) or a combination thereof, all of which are behaviorally equivalent. For example, modules may be implemented using computer hardware in combination with software routine(s) written in a computer language (Java, HTML, XML, PHP, Python, ActionScript, JavaScript, Ruby, Prolog, SQL, VBScript, Visual Basic, Perl, C, C++, Objective-C or the like). Additionally, it may be possible to implement modules using physical hardware that incorporates discrete or programmable analog, digital and/or quantum hardware. Examples of programmable hardware include: computers, microcontrollers, microprocessors, application-specific integrated circuits (ASICs), field programmable gate arrays (FPGAs), and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies may be used in combination to achieve the result of a functional module.

Some embodiments may employ processing hardware. Processing hardware may include one or more processors, computer equipment, embedded system, machines and/or the like. The processing hardware may be configured to execute instructions. The instructions may be stored on a machine-readable medium. According to some embodiments, the machine-readable medium (e.g. automated data medium) may be a medium configured to store data in a machine-readable format that may be accessed by an automated sensing device. Examples of machine-readable media include: magnetic disks, cards, tapes, and drums, flash memory, memory cards, electrically erasable programmable read-only memory (EEPROM), solid state drives, optical disks, barcodes, magnetic ink characters, and/or the like.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described example embodiments. In particular, it should be noted that, for example purposes, wearable systems have been described that may cause cessation of hemorrhages in a person, such as an injured soldier, law enforcement officer, or government agent. However, one skilled in the art will recognize that embodiments may be implemented that are applied to a subject after a wound is inflicted. Additionally, the subject may extend to animals and/or systems with flexible plumbing (e.g. a robotic system comprising at least one fluid).

In addition, it should be understood that any figures that highlight any functionality and/or advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112. Claims that do not expressly include the phrase "means for" or "step for" are not to be interpreted under 35 U.S.C. 112.

What is claimed is:

1. A wearable system comprising:
   a) a plurality of tourniquets, each of the plurality of tourniquets:
      i) comprising an inflatable chamber; and
      ii) configured to occlude blood flow in at least one artery of a wearer;
   b) a compressed gas source in fluid communication with the inflatable chamber of each of the plurality of tourniquets;
   c) a plurality of valves, each valve of the plurality of valves comprising:
      i) a valve input in fluid communication with the compressed gas source; and
      ii) a valve output in fluid communication with the inflatable chamber of one of the plurality of tourniquets;
   d) at least one fixed pressure regulator, each of the at least one fixed pressure regulator comprising:
      i) at least one regulator output in direct fluid communication with the valve input of at least one of the plurality of valves; and
      ii) a regulator input in direct fluid communication with the compressed gas source; each of the at least one fixed pressure regulator configured to receive at least one compressed gas from the compressed gas source and regulate a pressure of the at least one compressed gas delivered to the plurality of valves in fluid communication with the regulator output; and
   e) a plurality of switches, each of the plurality of switches configured to operate one of the plurality of valves after the plurality of tourniquets are fitted to the wearer.

2. The system according to claim 1, wherein the plurality of tourniquets are at least partially coupled to at least one of the following:
   a) a suit;
   b) a uniform;
   c) a piece of body armor; or
   d) an article of clothing.

3. The system according to claim 1, wherein the plurality of tourniquets are configured to be employed around at least one of the following locations:
   a) an arm;
   b) a forearm;
   c) an upper arm;
   d) a leg;
   e) a lower leg; or
   f) an upper leg.

4. The system according to claim 1, wherein at least one of the plurality of tourniquets is configured to be employed as a junctional tourniquet at one of the following locations:
   a) a shoulder;
   b) abdomen; or
   c) a groin.

5. The system according to claim 1, wherein the inflatable chamber is coupled to a pressure release valve.

6. The system according to claim 1, wherein the at least one fixed pressure regulator is configured for a distinct maximum pressure for each of at least two of the following:
   a) at least one of the plurality of tourniquets configured for an arm of the wearer;
   b) at least one of the plurality of tourniquets configured for a leg of the wearer;
   c) at least one of the plurality of tourniquets configured for a forearm of the wearer;
   d) at least one of the plurality of tourniquets configured for an upper arm of the wearer;
   e) at least one of the plurality of tourniquets configured for a lower leg of the wearer;
   f) at least one of the plurality of tourniquets configured for an upper leg of the wearer;
   g) at least one of the plurality of tourniquets tourniquet configured for a shoulder of the wearer;
   h) at least one of the plurality of tourniquets configured for a groin of the wearer; or
   i) at least one of the plurality of tourniquets configured for the abdomen of the wearer.

7. The system according to claim 1, wherein the at least one fixed pressure regulator is set within a range of 6-10 PSI.

8. The system according to claim 1, wherein at least one of the switches comprises a solenoid.

9. The system according to claim 1, further comprising a manifold comprising at least three ports in fluid communication with at least two of the plurality of tourniquets.

10. The system according to claim 1, further comprising a manifold comprising the compressed gas source.

11. The system according to claim 1, further comprising a plurality of check valves, each of the check valves:
   a) in fluid communication with the inflatable chamber of one of the plurality of tourniquets; and
   b) configured to prevent loss of at least a portion of the pressure in the inflatable chamber when pressurized.

12. The system according to claim 1, further comprising a physiological sensor and a processing unit, the processing unit configured to:
   a) receive a physiological signal from the physiological sensor; and
   b) communicate a command to one of the switches, the command based at least in part on the physiological signal.

13. The system according to claim 1, further comprising a plurality of physiological sensors, at least two of the sensors configured to communicate a physiological signal from two distinct locations on the body of the wearer.

14. The system according to claim 1, further comprising a receiving unit configured to receive at least one command wirelessly communicated from a remote device.

* * * * *